US009556301B1

(12) United States Patent
Jafar Mazumder et al.

(10) Patent No.: US 9,556,301 B1
(45) Date of Patent: Jan. 31, 2017

(54) CYCLOPOLYMER CONTAINING RESIDUES OF METHIONINE AND SYNTHESIS AND USES THEREOF

(71) Applicant: KING FAHD UNIVERSITY OF PETROLEUM AND MINERALS, Dhahran (SA)

(72) Inventors: Mohammad Abu Jafar Mazumder, Hamilton (CA); Hasan Ali Al-Muallem, Dhahran (SA); Shaikh Asrof Ali, West Midnapore (IN); Mohamad Khalid Estaitie, Jeddah (SA)

(73) Assignee: King Fahd Universoty of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/957,150

(22) Filed: Dec. 2, 2015

(51) Int. Cl.
  C08F 228/04  (2006.01)
  C07C 323/58  (2006.01)
  G01N 5/00    (2006.01)
  C23F 11/04   (2006.01)

(52) U.S. Cl.
  CPC ............ *C08F 228/04* (2013.01); *C07C 323/58* (2013.01); *C23F 11/04* (2013.01); *G01N 5/00* (2013.01)

(58) Field of Classification Search
  CPC ........ C08F 228/04; C07C 323/58; G01N 5/00; C23F 11/04
  USPC ........................................................ 524/547
  See application file for complete search history.

(56) References Cited

U.S. PATENT DOCUMENTS

2006/0193789 A1   8/2006   Tamarkin et al.
2007/0010573 A1   1/2007   Kong et al.

FOREIGN PATENT DOCUMENTS

IN          251149 B      3/2012
WO   2004/113275 A2     12/2004
WO   2006/052712 A1      5/2006
WO   2014/094412 A1      6/2014

OTHER PUBLICATIONS

Tawfik A. Saleh, et al., "A novel cross-linked pH-responsive tetrapolymer: Synthesis, characterization and sorption evaluation towards Cr(III)", Chemical Engineering Journal, vol. 269, 2015, pp. 9-19.*
Shamsuddeen A. Haladu, et al., "A pH-Responsive Cyclopolymer Having Phospho- and Sulfopropyl Pendents in the Same Repeating Unit: Synthesis, Characterization, and Its Application as an Antiscalant", Journal of Popymer Science, Part A: Polymer Chemistry, vol. 51, 2013, pp. 5130-5142.*
Shaikh A. Ali, et al., "Synthesis, solution properties and scale-inhibiting behaviour of a diallylammonium/sulfur dioxide cyclocopolymer bearing phospho- and sulfopropyl pendents", Polym. Int., vol. 63, 2014, pp. 1682-1690.*
Ali, S.A., et al., "A Novel Cyclopolymer Containing Residues of Essential Amino Acid Methionine: Synthesis and Application", URL: http://abstract.eurasia13.org/122-polymers-and-soft-matter/op-polymers-and-soft-matter/427-a-novel-cyclopolymer-containing-residues-of-essential-amino-acid-methionine-synthesis-and-application, 1 page total, (2014) (Abstract only).
Yokoyama, Y., et al., "Low-Capacity Cation-Exchange Chromatography of Amino Acids Using a Novel Sulfoacylated Macroreticular Polystyrene-Divinylbenzene Column with Binary Gradient Elution", URL: http://www.ncbi.nlm.nih.gov/pubmed/15352509, Anal Sci., vol. 20, No. 8, 2 pages total, (2004) (Abstract only).
Sieczkowska, B., et al., "New Photolabile Functional Polymers for Patterning onto Gold Obtained by Click Chemistry", URL: http://pubs.acs.org/doi/abs/10.1021/ma062410z Macromolecules, vol. 40, No. 7, 2 pages total, (2007) (Abstract only).
Al-Muallem, H.A., et al., "A Novel Cyclopolymer Containing Residues of Essential Amino Acid Methionine: Synthesis and Application", Iranian Polymer Journal, vol. 24, pp. 541-547, (2015).

* cited by examiner

*Primary Examiner* — Michael M Bernshteyn
(74) *Attorney, Agent, or Firm* — Oblon, McClelland, Maier & Neustadt, L.L.P.

(57) ABSTRACT

Cyclopolymers and N,N-diallyl methionine-based monomers or salts, solvates, tautomers or stereoisomers as corrosion inhibitors. A process for producing the cyclopolymers by Butler cyclopolymerization of the monomers in the presence of sulfur dioxide. In addition, a method for determining a percent inhibition efficiency of metal corrosion for the cyclopolymers and monomers as well as applications and methods for the cyclopolymers as coatings, compositions, and formulations for preventing metal corrosion.

14 Claims, 6 Drawing Sheets

CYCLOPOLYMER CONTAINING RESIDUES OF METHIONINE AND SYNTHESIS AND USES THEREOF

BACKGROUND OF THE INVENTION

Technical Field

The present disclosure relates to monomers and cyclocopolymers having an amino acid methionine-based structure as well as methods for their synthesis and preparation. Additionally, the present disclosure relates to applications of these monomers and cyclocopolymers as inhibitors of metallic corrosion.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Butler's cyclopolymerization protocol [Butler G B (1992) Cyclopolymerization and cyclocopolymerization, Marcel Dekker, New York, N.Y., USA; and Kudaibergenov S, Jaeger W, Laschewsky A (2006) Polymeric betaines: Synthesis, characterization, and application. Adv. Polym. Sci., 201:157-224; and Singh P K, Singh V K, Singh M (2007) Zwitterionic polyelectrolytes: A review. E-Polymers 030:1-34; and Jaeger W, Bohrisch J, Laschewsky A (2010) Synthetic polymers with quaternary nitrogen atoms—synthesis and structure of the most used type of cationic polyelectrolytes. Prog. Polym. Sci 35:511-577—each incorporated herein by reference in its entirety] involving diallylammonium salts has led to a plethora of industrially significant pyrrolidine ring-embedded cyclopolymers whose architecture is considered to be the eighth most important structural type [Butler G B (2000) Cyclopolymerization. J. Polym. Sci. Part A: Polym. Chem 38:3451-3461; and McGrew F C (1958) Structure of synthetic high polymers. J. Chem. Educ 35:178-186. —each incorporated herein by reference in its entirety]. Butler's cyclopolymer poly(diallyldimethylammonium chloride) has numerous publications and patents (>1000) and over 35 million pounds of it alone are sold per year for water purification and personal care formulations. Numerous diallylammonium monomers have also been copolymerized with $SO_2$ to give value added products [Ali S A, Al-Hamouz O C S (2012) Comparative solution properties of cyclocopolymers having cationic, anionic, zwitterionic and zwitterionic/anionic backbones of similar degree of polymerization. Polymer 53:3368-3377; and Abu-Thabit N Y, Kazi I W, Al-Muallem H A, Ali S A (2011) Phosphonobetaine/sulfur dioxide copolymer by Butler's cyclopolymerization process. Eur. Polym. J 47:1113-1123; and Ali S A, Umar Y, Abu-Sharkh B F, Al-Muallem H A (2006) Synthesis and comparative solution properties of single-, twin-, and triple-tailed associating ionic polymers based on diallylammonium salts. J. Polym. Sci. Part A Polym. Chem 44:5480-5494. —each incorporated herein by reference in its entirety].

One objective in the field is to examine the efficacy of functional motifs of trivalent amine and sulfide in a polymer backbone in arresting metal corrosion. Inhibition of metal corrosion by organic inhibitors is influenced by the presence of heteroatoms whose efficacies are known to increase in the order O<N<S<P [Kiani M A, Mousavi M F, Ghasemi S, Shamsipur M, Kazemi S H (2008) Inhibitory effect of some amino acids on corrosion of Pb—Ca—Sn alloy in sulfuric acid solution. Corros. Sci 50:1035-1045. —incorporated herein by reference in its entirety]. The inhibitor molecules interfere with anodic and cathodic reactions occurring on the metal surfaces, and thus arrest or minimize the corrosion process [Revie W, Uhlig H H (2008) Corrosion and Corrosion Control: An Introduction to Corrosion Science and Engineering, Wiley-Interscience, NY, USA; and Sastri V S (1998) Corrosion Inhibitors, Principles and Application, John Wiley and Sons, USA—each incorporated herein by reference in its entirety]. The greater polarizability of the lone pair of electrons in the third period elements makes them better inhibitors as a result of formation of coordinate-type bonds to cover and safeguard the metal surface.

Available at low cost, the non-toxic amino acid methionine is attractive as a green inhibitor of mild steel corrosion since it contains three important heteroatoms: N, O and S. The methionine at a concentration of 25 ppm has been shown to impart 47% inhibition of mild steel corrosion in 0.1 M HCl at 25° C. [Zor S, Kandemirli F, Bingul M (2009) Protection of Metals and Physical Chemistry of Surfaces, Pleiades Publishing Ltd, Moscow, Russia. —incorporated herein by reference in its entirety]. At respective concentrations of 149, 165, and 181 ppm of methionine, methionine sulfoxide and methionine sulfone, the inhibition efficiency (IE) against copper corrosion in 1 M $HNO_3$ have been determined to be 79%, 85% and 88% [Khaled K F (2010) Corrosion control of copper in nitric acid solutions using some amino acids—A combined experimental and theoretical study. Corros. Sci 52:3225-3234. —incorporated herein by reference in its entirety]. In corrosive environments of 1 M HCl at 30° C. and 2 M HCl at 25° C. containing 149 ppm of methionine and 1000 ppm of glutaraldehyde-methionine condensation product, respectively, the corresponding IE of mild steel corrosion are reported to be 89% and 84% [Shanmugasundaram P, Sumathi T, Chandramohan G, Ramesh-Bapu G N K (2013) Corrosion inhibition study of 1062 grade a-low carbon steel in 1M HCl by L-methionine-weight loss, ICP-OES and SEM-EDX studies. Int. J. Curr. Res 5:2183-2191; and Rajappa S K, Venkatesha T V (2002) New condensation products as corrosion inhibitors for mild steel in a hydrochloric acid medium. Ind. J. Eng. Mater. Sci. 9:213-217. —each incorporated herein by reference in its entirety].

The use of methionine as a green corrosion inhibitor has thus achieved modest inhibition efficiencies. The industry demands much greater efficacies, on the order of 99% or more. Corrosion is a large concern in terms of cost, safety, health and environmental aspects and has become an increasing priority in both industry and society [Panah N B, Payehghadr M, Danaee I, Nourkojouri H, Sharbatdaran M (2012) Investigation of corrosion performance of epoxy coating containing polyaniline nanoparticles. Iran Polym J 21(11):747-754; and Amirshaqaq N, Salami-Kalajahi M, Mandavian M (2014) Corrosion behavior of aluminum/silica/polystyrene nanostructured hybrid flakes. Iran Polym J 23(9):699-706—each incorporated herein by reference in its entirety]. Even an improvement of 1% efficacy translates into a considerable savings. Polymers typically undergo stronger adsorption onto metal surface because of multiple anchoring sites, and thus exhibit better inhibition efficiencies than their monomeric analogs [Ulman, R. (1964) in Encyclopedia of Polymer Science and Technology; Vol. 1, (Eds: Mark, H. F.; Gaylord, N. G.; Bikales, N. M.), Interscience, New York, USA; and Annand R R, Hurd R M, Hackerman N (1965) Adsorption of Monomeric and Polymeric Amino Corrosion Inhibitors on Steel. J. Electrochem. Soc 112:138-144; and Bacskai R, Schroeder A H, Young D C (1991)

Hydrocarbon-soluble alkaline/formalin/formaldehyde oligomers as corrosion inhibitors. J. Appl. Polym. Sci 42:2435-2441. —each incorporated herein by reference in its entirety].

In view of the forgoing, one object of the present disclosure is to provide cyclopolymers containing residues of methionine keeping intact the integrity of its sulfide motifs and unquenched nitrogen valency (i.e. a trivalent N with its lone pair of electrons). This includes the synthesis of the potentially green novel monomer as well as the first time use of Butler's cyclopolymerization protocol for the formation of its cyclocopolymers having residue of essential amino acid methionine in each repeating unit. In addition to the monomers, cyclopolymers and methods for their preparation, the present disclosure further aims to provide methods for evaluating their efficacies in arresting metal corrosion, such as mild steel corrosion in 1 M HCl. A further aim of the present disclosure, is to provide a method for preventing or inhibiting metal corrosion comprising treatment with the cyclopolymers as well as metallic materials comprising the cyclopolymers in or on said metallic materials.

BRIEF SUMMARY OF THE INVENTION

According to a first aspect, the present disclosure relates to a cyclopolymer of formula (I)

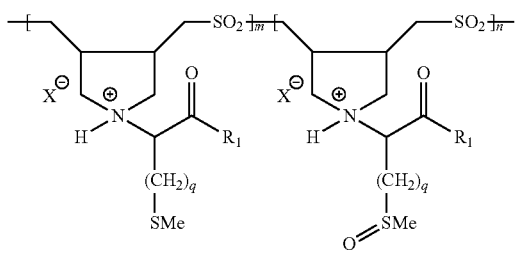

(I)

or a salt, solvate, tautomer, or stereoisomer thereof wherein i) $R_1$ is —H, —OH, —NH$_2$, —OR$_2$, —NHR$_2$, or NR$_2$R$_3$, ii) $R_2$ and $R_3$ are independently an optionally substituted alkyl, optionally substituted cycloalkyl, or optionally substituted aryl, iii) m is a whole number greater than zero, iv) n is a whole number greater than or equal to zero, v) q is a whole number in the range of 1-10, and vi) X is a counter ion.

In one embodiment, $R_1$ is —OCH$_2$CH$_3$, $R_2$ is —CH$_2$CH$_3$, q is 2, X is Cl and the compound of formula (I) is compound 1

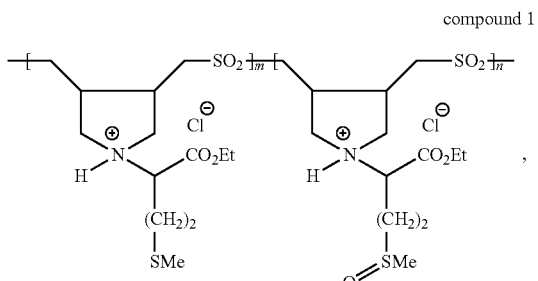

wherein m and n are independently whole numbers greater than zero.

In one embodiment, $R_1$ is —OCH$_2$CH$_3$, $R_2$ is —CH$_2$CH$_3$, q is 2, X is Cl and the compound of formula (I) is compound 2

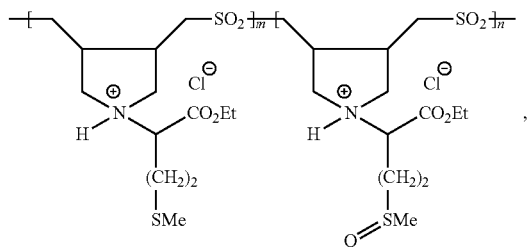

wherein m is a whole number greater than zero and n is equal to zero.

In one embodiment, the ratio of m:n is in the range of 10:1 to 1:10.

In one embodiment, the cyclopolymer has an intrinsic viscosity in the range of 0.125-0.300 dL g$^{-1}$ in a solution comprising 0.125-1 wt % of the cyclopolymer relative to the total weight of the solution.

In one embodiment, the cyclopolymer is soluble in water, soluble in methanol, or both.

In one embodiment, the cyclopolymer has a corrosion inhibition efficiency (% IE) in the range of 25-99% when the cyclopolymer is contacted to a metal surface at a concentration ranging from 0.10-125 ppm.

In one embodiment, the cyclopolymer has a free energy of adsorption ($\Delta G°_{ads}$) in the range of –30 to –70 kJ mol$^{-1}$ by a Langmuir adsorption isotherm.

According to a second aspect, the present disclosure relates to a N,N-diallyl methionine-based monomer of formula (II)

(II)

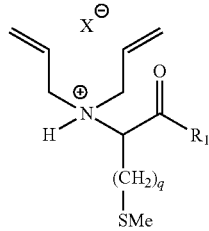

or a salt, solvate, tautomer, or stereoisomer thereof wherein $R_1$ is —H, —OH, —NH$_2$, —OR2, —NHR$_2$, or —NR$_2$R$_3$, ii) $R_2$ and $R_3$ are independently an optionally substituted alkyl, optionally substituted cycloalkyl or optionally substituted aryl, iii) q is a whole number in the range of 1-10, and iv) X is a counterion.

In one embodiment, $R_1$ is —OCH$_2$CH$_3$, $R_2$ is —CH$_2$CH$_3$, q is 2, X is Cl and the N,N-diallyl methionine-based monomer of formula (II) is compound 3

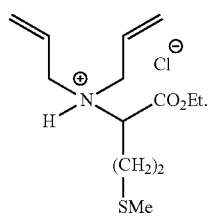

In one embodiment, the N,N-diallyl methionine-based monomer has a corrosion inhibition efficiency (% IE) in the range of 25-95% when the N,N-diallyl methionine-based monomer is contacted to a metal surface at a concentration ranging from 0.10-125 ppm.

According to a third aspect, the present disclosure relates to a process for producing the cyclopolymer comprising i) reacting a methionine-based salt with an allyl halide to form a diallyl methionine compound, ii) treating the diallyl methionine compound with an acid to form a N,N-diallyl methionine-based monomer, and iii) cyclocopolymerizing the N,N-diallyl methionine-based monomer using a free radical initiator in a solvent in the presence of sulfur dioxide.

In one embodiment, the cyclocopolymerizing is a Butler cyclopolymerization reaction and the free radical initiator is azobisisobutyronitrile (AIBN).

In one embodiment, the solvent comprises dimethyl sulfoxide and the process produces the cyclopolymer of formula (I) wherein m and n are independently whole numbers greater than zero.

In one embodiment, the solvent comprises ethanol, acetone, or both and the process produces the cyclopolymer of formula (I) wherein m is a whole number greater than zero and n is equal to zero.

According to a fourth aspect, the present disclosure relates to a method for determining a % inhibition efficiency of metal corrosion for the cyclopolymer comprising i) weighing a first metal sample before immersion into a first aqueous acid solution to obtain a first blank weight ($FW_B$) and after immersion into the first aqueous acid solution to obtain a second blank weight ($SW_B$), ii) weighing a second metal sample substantially the same as the first metal sample before immersion into a second aqueous acid solution to obtain a first inhibitor weight ($FW_1$) and after immersion into the second aqueous acid solution to obtain a second inhibitor weight ($SW_1$), and iii) determining the % inhibition efficiency according to formula (III):

$$\text{Inhibition Efficiency (\%)} = \frac{(FW_B - SW_B) - (FW_I - SW_I)}{(FW_B - SW_B)} \times 100\% \quad \text{(III)}$$

wherein, the first aqueous acid solution and second aqueous acid solution are substantially the same except that the second aqueous acid solution comprises 0.1-125 ppm of the cyclopolymer.

In one embodiment, the first metal sample and the second metal sample comprise steel and the first acidic solution and the second acidic solution comprise 0.5-2.0 M HCl.

In one embodiment, the first metal sample and the second metal sample are immersed for 2-8 hours at a temperature of 20-100° C.

According to a fifth aspect, the present disclosure relates to a method for protecting metallic materials from corrosion, comprising treating the metal with the cyclopolymer.

According to a sixth aspect, the present disclosure relates to a metallic material comprising the cyclopolymer, wherein the cyclopolymer is present in or on said metallic material.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
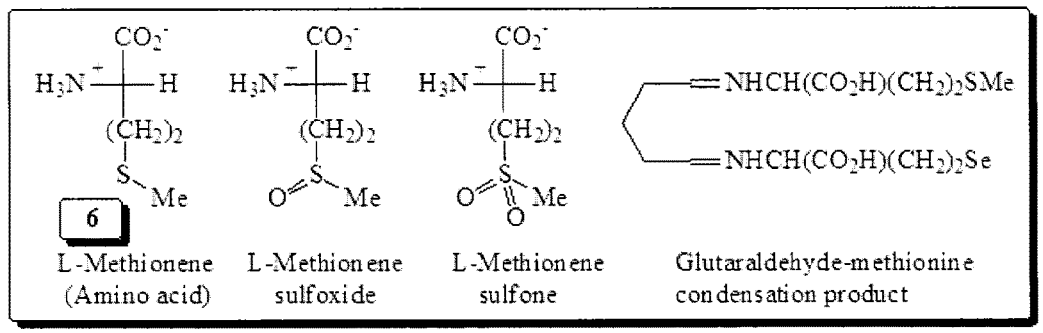
FIG. 1 is residues based upon the essential amino acid methionine, compound 6.

Referring now to the drawings. Embodiments of the present disclosure will now be described more fully hereinafter with reference to the accompanying drawings, in which some, but not all of the embodiments of the disclosure are shown. The present disclosure will be better understood with reference to the following definitions.

As used herein a "polymer" refers to a large molecule, or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer or resin whose repetition would produce the complete polymer chain (excluding the end groups) by linking the repeat units together successively along the chain. The process by which monomers combine end to end to form a polymer is referred to herein as "polymerization", monomers are molecules which can undergo polymerization, thereby contributing constitutional repeating units to the essential structures of a macromolecule or polymer. As used herein a "copolymer" refers to a polymer derived from more than one species of monomer and are obtained by the "copolymerization" of more than one species of monomer. Copolymers obtained by copolymerization of two monomer species may be termed bipolymers, those obtained from three monomers may be termed terpolymers and those obtained from four monomers may be termed quaterpolymers, etc. As used herein a "cyclopolymer" refers to a polymer having cyclic structures in the main polymer chain (i.e. the polymer backbone) and are obtained by the "cyclopolymerization" of appropriate monomers where one or more cyclic or ring structures, heterocyclic or homocyclic, are formed. In many cases, the cyclic structures may be formed during the cyclopolymerization which may proceed by an alternating intra-intermolecular chain mechanism for polymerization. As used herein a "cyclocopolymer" refers to a polymer sharing the definition of a copolymer and a cyclopolymer and may be formed by "cyclocopolymerization".

As used herein, the terms "compound" and "complex" refer to a chemical entity, whether in the solid, liquid or gaseous phase, as well as in a crude mixture or purified and isolated form. The chemical transformations and/or reactions described herein are envisaged to proceed via standard laboratory and experimental techniques in regard to performing the reaction as well as standard purification, isolation and characterization protocols known to those skilled in the art.

As used herein, the term "salts" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts include, but are not limited to, the conventional non-toxic salts or the quaternary ammonium salts of the parent compound formed, for example, from non-toxic inorganic or organic acids. Exemplary conventional non-toxic salts include those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic and mixtures thereof and the like. Further, salts of carboxylic acid containing compounds may include cations such as lithium, sodium, potassium, magnesium, quaternary ammonium, and the like. The salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "solvate" refers to a physical association of a compound, monomer or polymer of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic acid tautomerism in heterocyclic rings), enamine and enamine and anomers of reducing sugars.

Prototropy or prototropic tautomerism refers to the relocation of a proton. Prototropy may be considered a subset of acid base behavior. Prototropic tautomers are sets of isomeric protonation states with the same empirical formula and total charge. Tautomerizations may be catalyzed by bases (deprotonation, formation of an enolate or delocalized anion, and protonation at a different position of the anion) and/or acids (protonation, formation of a delocalized cation and deprotonation at a different position adjacent to the cation). Two additional subcategories of tautomerization include annular tautomerism, wherein a proton can occupy two or more positions of a heterocyclic system, and ring-chain tautomerism, wherein the movement of a proton is accompanied by a change from an open structure to a ring. Valence tautomerism is a type of tautomerism in which single and/or double bonds are rapidly formed and ruptured, without migration of atoms or groups. It is distinct from prototropic tautomerism, and involves processes with rapid reorganization of bonding electrons, such as open and closed forms of certain heterocycles, such as azide-tetrazole or mesoionic munchnone-acylamino ketene. Valence tautomerism requires a change in molecular geometry unlike canonical resonance structures or mesomers. In terms of the present disclosure, the tautomerism may refer to prototropic tautomerism, annular tautomerism, ring-chain tautomerism, valence tautomerism, or mixtures thereof.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection or their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which thy rotate polarized light and how they interact with different optical isomers of other compounds. Diastereomers and stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers or both.

Conformers (rotamers), or conformational isomerism refers to a form of isomerism that describes the phenomenon of molecules with the same structural formula but with different shapes due to rotations about one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation about the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted hetercyclyl and mixtures thereof and the like.

As used herein, the term "alkyl" unless otherwise specified, refers to both branched and straight chain saturated aliphatic primary, secondary, and/or tertiary hydrocarbons of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

According to a first aspect, the present disclosure relates to a cyclopolymer of formula (I)

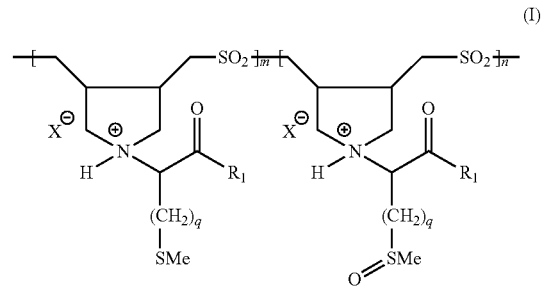

(I)

or a salt, solvate, tautomer, or stereoisomer thereof wherein i) $R_1$ is —H, —OH, —$NH_2$, —$OR_2$, —$NHR_2$, or $NR_2R_3$, ii) $R_2$ and $R_3$ are independently an optionally substituted alkyl, optionally substituted cycloalkyl, or optionally substituted aryl, iii) m is a whole number greater than zero, iv) n is a whole number greater than or equal to zero, v) q is a whole number in the range of 1-10, and vi) X is a counter ion.

In a preferred embodiment, $R_1$ is —H, —OH, —$NH_2$, —$OR_2$, —NHR, or $NR_2R_3$, preferably $R_1$ is —H, —OH, —$OCH_3$, or $OCH_2CH_3$, most preferably $R_1$ is —$OCH_2CH_3$. In a preferred embodiment, m is a whole number greater than zero, preferably m is 1-5000, preferably 1-2500, preferably 1-1000, preferably 1-500, preferably 2-400, preferably 3-300, preferably 4-275, preferably 5-250, preferably 10-200, preferably 15-150, preferably 20-100, preferably 25-50. In a preferred embodiment, n is a whole number greater than or equal to zero, preferably n is 0-5000, preferably 0-2500, preferably 0-1000, preferably 0-500, preferably 0-400, preferably 0-300, preferably 0-275, preferably 5-250, preferably 10-200, preferably 15-150, preferably 20-100, preferably 25-50. In a preferred embodiment, q is a whole number in the range of 1-10, preferably 1-8, preferably 1-5, preferably 1-3, most preferably 2. In one embodiment, the value of q denotes a straight alkyl chain of $CH_2$ groups, it is equally envisaged that this alkyl chain moiety may be optionally substituted as described herein. In a preferred embodiment, X is a counter ion, preferably $F^-$, $Cl^-$, $Br^-$, $I^-$, $NO_3^-$, $OH^-$ or other suitable monoanion, preferably a halide, most preferably $Cl^-$. In another embodiment, it is equally envisaged that the pyrrolidine ring moiety of the cyclopolymer of formula (I) may be optionally substituted as described herein. It is equally envisaged that the cyclopolymer of formula (I) may have properties that fall outside of these preferred ranges and still provide suitable cyclopolymer of formula (I) material.

In a preferred embodiment, the ratio of m:n is in the range of 10:1 to 1:10, preferably 5:1 to 1:5, preferably 2:1 to 1:2, preferably 1.5:1 to 1:1.5 or 1:1. In a preferred embodiment, the ratio of m:n is approximately 1:1. In another embodiment the ratio of m:n may be envisaged to be 1:1.1, preferably 1:1.25, preferably 1:1.5, preferably 1:1.75, preferably 1:2, preferably 1:2.5, preferably 1:5, preferably 1:10. In another embodiment, the ratio of m:n may be envisaged to be 1.1:1, preferably 1.25:1, preferably 1.5:1, preferably 1.75:1, preferably 2:1, preferably 2.5:1, preferably 5:1, preferably 10:1. The repeating unit m, the repeating unit n, or both the repeating unit m and n may be repeated in the cyclopolymer of formula (I) from 10-10000 times, preferably 20 to 5000 times, more preferably 25 to 2500 times, more preferably 50 to 1500 times, more preferably 100 to 1000 times. It is equally envisaged that values for m, n, or both may fall outside of these ranges and still provide suitable cyclopolymer of formula (I) material.

In a preferred embodiment, $R_1$ is —$OCH_2CH_3$, $R_2$ is —$CH_2CH_3$, q is 2, X is $Cl^-$ and the cyclopolymer of the present disclosure and compound of formula (I) is

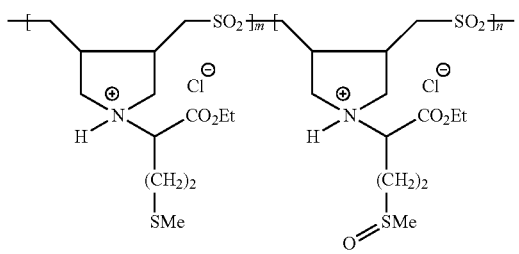

compound 1 wherein m and n are independently whole numbers greater than zero, preferably 1-5000, preferably 1-2500, preferably 1-1000, preferably 1-500, preferably 2-400, preferably 3-300, preferably 4-275, preferably 5-250, preferably 10-200, preferably 15-150, preferably 20-100, preferably 25-50.

In one embodiment, $R_1$ is —$OCH_2CH_3$, $R_2$ is —$CH_2CH_3$, q is 2, X is a and the cyclopolymer of the present disclosure and compound of formula (I) is

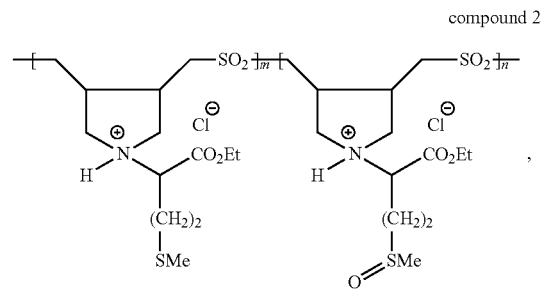

compound 2 wherein m is a whole number greater than zero, preferably 1-5000, preferably 1-2500, preferably 1-1000, preferably 1-500, preferably 2-400, preferably 3-300, preferably 4-275, preferably 5-250, preferably 10-200, preferably 15-150, preferably 20-100, preferably 25-50, and n is equal to zero. Thus, an alternate chemical representation of the compound of formula (I) is

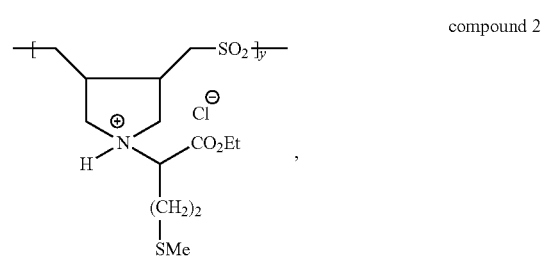

compound 2 wherein y is a whole number greater than zero, preferably 1-5000, preferably 1-2500, preferably 1-1000, preferably 1-500, preferably 2-400, preferably 3-300, preferably 4-275, preferably 5-250, preferably 10-200, preferably 15-150, preferably 20-100, preferably 25-50.

The present disclosure provides cyclopolymers, preferably copolymers and/or terpolymers where one or more of the monomers constituting the copolymer each contain one or more tertiary or quaternary nitrogen atoms or tertiary or quaternary ammonium cations. These tertiary or quaternary ammonium salt monomers are preferably neutral and zwitterionic, where positive and negative electrical charges are present in each monomeric molecule at equal amounts. In a preferred embodiment, the copolymer has a least one tertiary or quaternary ammonium salt monomer that is a methionine-based derivative monomer.

According to a second aspect, the present disclosure relates to a N,N-diallyl methionine-based monomer of formula (II)

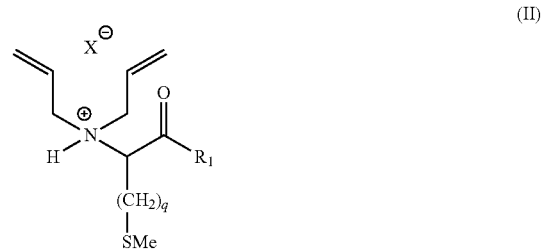

(II)

or a salt, solvate, tautomer, or stereoisomer thereof wherein $R_1$ is —H, —OH, —NH$_2$, —OR2, —NHR$_2$, or —NR$_2$R$_3$, ii) $R_2$ and $R_3$ are independently an optionally substituted alkyl, optionally substituted cycloalkyl or optionally substituted aryl, iii) q is a whole number in the range of 1-10, and iv) X is a counterion. In a preferred embodiment, $R_1$ is —H, —OH, —OCH$_3$, or —OCH$_2$CH$_3$, most preferably $R_1$ is —OCH$_2$CH$_3$. In a preferred embodiment, q is a whole number in the range of 1-10, preferably 1-8, preferably 1-5, preferably 1-3, most preferably 2. In a preferred embodiment, X is a counter ion, preferably F$^-$, Cl$^-$, Br$^-$, I$^-$, NO$_3^-$, OH$^-$ or other suitable monoanion, preferably a halide, most preferably Cl$^-$.

In one embodiment, $R_1$ is —OCH$_2$CH$_3$, $R_2$ is —CH$_2$CH$_3$, q is 2, X is Cl$^-$ and the N,N-diallyl methionine-based monomer of formula (II) is

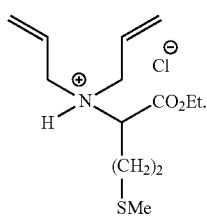

compound 3

In a preferred embodiment, monomers of the copolymer or cyclocopolymer include, but are not limited to N,N-diallylmethionine ethyl ester hydrochloride (compound 3) and sulfur dioxide (SO$_2$, O=S=O). In a preferred embodiment when cyclocopolymerized into a copolymer every two monomers of formula (II) are connected by a sulfur dioxide molecule. In certain embodiments, the monomer represented by formula (II) may be sulfonized prior to or during the cyclopolymerization. In another embodiment, it is equally envisaged that the cyclopolymer of the present disclosure, in addition to the monomer of formula (II) and sulfur dioxide may further comprise at least one selected from the group including, but not limited to, a monomer having a mono-, di-, tri- or tetrallyl group, a monomer having one or more sulfoxide or sulfone functional groups, a monomer containing one or more quaternary or tertiary nitrogen atoms that are optionally part of a 3- to 8-membered heterocyclic ring, nitrogen dioxide, nitrogen disulfide, carbon dioxide, carbon disulfide and mixtures thereof.

In another embodiment, the cyclopolymer of the present disclosure may further comprise one or more "cross-linking" elements. As used herein, "cross-linking" refers to polymers and resins containing branches that connect polymer chains via covalent bonds. The cross-linking can alter the physical and mechanical properties of the polymer. Cross-linking may be formed by chemical reactions that are initiated by heat, pressure, change in pH, and/or radiation, with or without the presence of a cross-linking agent and/or catalyst.

Since a copolymer consists of at least two types of constituent units (structural units), copolymers can be classified based on how these units are arranged along the chain. Alternating copolymers are copolymers consisting of macromolecules comprising two species of monomeric units in a regular alternating sequence. An alternating copolymer may be considered as a homopolymer derived from an implicit or hypothetical monomer. A periodic copolymer is a copolymer which has two species of monomeric units arranged in a repeating sequence. A statistical copolymer is a copolymer in which the sequence of monomeric units follows a statistical rule. Alternatively if the probability of finding a specific monomeric unit at a particular point in the chain is equal to the mole fraction of that monomeric unit in the chain, then the polymer may be referred to as a truly random copolymer. In gradient copolymers the monomer composition changes gradually along the chain. The cyclopolymer of the present disclosure may be an alternating copolymer, a periodic copolymer, a statistical copolymer a random copolymer or mixtures thereof.

Copolymers may also be described in terms of the existence of or arrangement of branches in the polymer structure. Linear copolymers consist of a single main chain whereas branched copolymers consist of a single main chain with one or more polymeric side chains. The cyclopolymer of the present disclosure may be a linear copolymer, a branched copolymer, other special types of branched copolymers including star copolymers, brush copolymers and comb copolymers and mixtures thereof.

A block copolymer is a specific type of copolymer made up of blocks of different polymerized monomers. In a block copolymer, a portion of the macromolecule comprising many constitutional units has at least one feature which is not present in the adjacent portions. Block copolymers comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers respectively, tetrablocks and multiblocks, etc. can also be fabricated. In stereoblock copolymers a special structure can be formed from one monomer where the distinguishing feature is the tacticity of each block. The cyclopolymer of the present disclosure may be a block copolymer, a stereoblock copolymer or mixtures thereof.

A graft macromolecule refers to a macromolecule with one or more species of block connected to the main chain as side chains, these side chains having constitutional or configurational features that differ from those in the main chain. Graft copolymers are a specific type of branched copolymer in which the side chains are structurally distinct from the main chain. For example, the main chain and side chains may be composed of distinct homopolymers; however, the individual chains of a graft copolymer may be homopolymers or copolymers. Different copolymer sequencing is sufficient to define a structural difference, thus a diblock copolymer with alternating copolymer side chains may be termed a graft copolymer. As with block copolymers, the quasi-composite graft copolymer product has properties of both "components". The cyclopolymer of the present disclosure may be a graft copolymer.

Polymers can be classified based on their tacticity or structure. Tacticity may be defined as the geometric arrangement (orientation) of the characteristic group (side group or side chain) of monomer units or repeating units with respect to the main chain (backbone) of the polymer. An isotactic polymer is the type of polymer in which the characteristic groups are arranged on the same side of the main chain. A syndiotactic polymer is the type of polymer in which the characteristic groups are arranged in an alternating fashion. An atactic polymer is the type of polymer in which the characteristic groups are arranged in irregular fashion (randomness) around the main chain. The cyclopolymer of the present disclosure may be isotactic, syndiotactic, atactic or copolymers and mixtures thereof.

The degree of polymerization (DP) is defined as the number of monomeric units in a macromolecule or polymer. In one embodiment, the cyclopolymer of the present disclosure has a degree of polymerization of 100-2500, preferably 100-1500, preferably 100-750, preferably 100-300. In a preferred embodiment, the cyclopolymer of the present disclosure is produced by free radical polymerization which often results in a wide molecular weight distribution. In one embodiment, the cyclopolymer of the present disclosure has an average molecular weight of 5-200 kDa, preferably 10-150 kDa, preferably 10-100 kDa, preferably 10-75 kDa, more preferably 10-50 kDa, preferably 20-35 kDa.

Dispersity is a measure of the heterogeneity of sizes of molecules or particles in a mixture. The polydispersity index (PDI or heterogeneity index) is a measure of the distribution of molecular mass in a given polymer sample. The PDI is calculated as the weight average molecular weight divided by the number average molecular weight. Typically, dispersities vary based on the mechanism of polymerization and can be affected by a variety of reaction conditions such as reactant ratios, how close the polymerization went to completion, etc. Generally, a decreasing molecular weight distribution increases water solubility and increases flexibility; it can further affect properties including crystalizability, adhesion, mechanical strength and diffusivity. In one embodiment, the cyclopolymer of the present disclosure has a PDI of at least 1 and up to 6, preferably up to 5, preferably up to 3, preferably up to 2.5, preferably up to 2, preferably up to 1.5, preferably up to 1.25.

General grades of the cyclopolymer of the present disclosure may include ultra-low viscosity (DP <300 and average molecular weight <25 kDa), low viscosity (DP ~350-650 and average molecular weight of ~30-50 kDa), medium viscosity (DP ~1000-1500 and average molecular weight ~80-125 kDa), and high viscosity (DP ~1600-2200 and average molecular weight ~150-190 kDa). The cyclopolymer of the present disclosure may be ultra-low viscosity, low viscosity, medium viscosity, high viscosity or mixtures thereof.

Intrinsic viscosity [η] is a measure of a solute's contribution to the viscosity (η) of a solution. It is distinct from inherent viscosity, which is the ratio of the natural logarithm of the relative viscosity to the mass concentration of a polymer. Intrinsic viscosity is often defined by formula (IV).

$$\lim_{\phi \to 0} \frac{\eta - \eta_0}{\eta_0 \phi} \tag{IV}$$

In this formula, $\eta_0$ is the viscosity in the absence of the solute and $\phi$ is the volume fraction of the solute in the solution. Often, the intrinsic viscosity [η] is a dimensionless number. In other instances, $\phi$ is usually solute mass concentration (c, g/dL), and the units of intrinsic viscosity [η] are deciliters per gram (dL/g), otherwise known as inverse concentration. In a preferred embodiment the cyclopolymer of the present disclosure has an intrinsic viscosity of 0.125-0.300 dL g$^{-1}$, preferably 0.150-0.275, preferably 0.175-0.250, preferably 0.175-0.235, preferably 0.190-0.210 dL g$^{-1}$ when measured as 0.1-2 wt % solutions, preferably 0.125-1 wt % solutions and preferably the intrinsic viscosity is determined with an Ubbelohde viscometer.

In general, polymeric mixtures are far less miscible than mixtures of small molecules. This is a result of the driving force for mixing usually being entropy, rather than interaction energy. Miscible materials generally form a solution not because their interaction with each other is more favorable than their self-interaction, but because of an increase in entropy and hence free energy associated with increasing the amount of volume available to each component. This tends to increase the free energy of mixing for much larger polymeric molecules in polymer solutions and thus makes solvation less favorable. In dilute solution, the properties of the polymer are characterized by the interaction between the solvent and the polymer. In a good solvent, the polymer appears swollen and occupies a large volume, the intermolecular forces between the solvent and monomer subunits dominate over intramolecular interactions. In a bad solvent or poor solvent, intramolecular forces dominate and the chain contracts.

Miscibility can be estimated by using solubility parameters (δ), which are tabulated for many different polymers and solvents. The Hildebrand solubility parameter provides a numerical estimate of the degree of interaction between materials, and can be a good indication of solubility, particularly for materials such as polymers. Materials with similar values of δ are likely to be miscible. In a preferred embodiment, the cyclopolymer of the present disclosure is soluble in water (δ=23.4 (cal/cm$^3$)$^{1/2}$), soluble in methanol (δ=14.5 (cal/cm$^3$)$^{1/2}$), or both. In a preferred embodiment, the cyclopolymer of the present disclosure has a Hildebrand solubility parameter of 5-25 (cal/cm$^3$)$^{1/2}$, preferably 8-22 (cal/cm$^3$)$^{1/2}$, more preferably 10-20 (cal/cm$^3$)$^{1/2}$. In a preferred embodiment, the cyclopolymer of formula (I) wherein m and n are independently whole numbers greater than zero (i.e. compound 1) is water soluble. In a preferred embodiment, the cyclopolymer of formula (I) wherein m is a whole number greater than zero and n is equal to zero (i.e. compound 2) may be water insoluble but soluble in methanol.

According to a third aspect, the present disclosure relates to a process for producing the cyclopolymer of formula (I) in any of their embodiments. In addition, the process described herein is envisaged to additionally produce the N,N-diallyl methionine-based monomer of formula (II) in any of their embodiments.

In one step of the process, a methionine-based salt is reacted with an allyl halide to form a diallyl methionine compound. In a preferred embodiment, the reaction is an allylation, a chemical reaction that adds an allyl group to a substrate; preferably the reaction is a diallylation, a chemical reaction that adds two allyl groups to a substrate, most preferably a N,N-diallylation. In a preferred embodiment, the methionine based salt has the basic structure of the essential amino acid methionine including D-methionine, L-methionine, and/or DL-methionine, preferably the methionine based salt is an ammonia salt of the compound of formula (II) lacking the allyl groups, preferably a methionine ester salt, most preferably a methionine ethyl ester salt or methionine ethyl ester hydrochloride. In a preferred embodiment, the allyl halide is one selected from the exemplary group including, but not limited to, allyl bromide, allyl chloride, allyl iodide, allyl triflate, preferably allyl bromide. In a preferred embodiment, the allylation reaction is performed in the presence of a base. The base may be a strong base (i.e. lithium hydroxide, sodium hydroxide, potassium hydroxide, etc.) or a weak base (i.e. potassium carbonate, ammonium hydroxide, sodium carbonate, calcium carbonate, sodium sulfate), preferably a weak base, most preferably potassium carbonate.

In a preferred embodiment, the allylation reaction is performed in a polar aprotic solvent selected from the exemplary group including, but not limited to, tetrahydrofuran, ethyl acetate, acetone, dimethyl formamide, acetonitrile, dimethyl sulfoxide, nitromethane, most preferably acetonitrile. It is equally envisaged that the allylation reaction may be adapted to be performed in a non-polar solvent, a polar protic solvent or mixtures thereof. In a preferred embodiment, the allylation reaction is performed under an inert environment (i.e. under $N_2$ or Ar gas, preferably $N_2$). In a preferred embodiment, the allylation reaction is performed at a temperature of 0-80° C., preferably 20-75° C., preferably 30-70° C., preferably 40-65° C., preferably 45-60° C. or 50° C. and has a stirred reaction time of 2-48 hr, preferably 4-36 hr, preferably 8-30 hr, preferably 10-28 hr, preferably 12-24 hr, preferably 18-24 hr. In a preferred embodiment, the allylation reaction has a yield of greater than 50%, preferably greater than 60%, preferably greater than 70%, more preferably greater than 75%.

In one step of the process, the diallyl methionine compound is treated with an acid to form a N,N-diallyl methionine-based monomer, preferably a compound of formula (II), most preferably compound 3. In a preferred embodiment, the acid is at least one selected from the group consisting of mineral acids (inorganic acids), sulfonic acids (RS(=O)$_2$—OH), carboxylic acids (R—C(O)OH), halogenated carboxylic acids and mixtures thereof, preferably a carboxylic acid or mineral acid, most preferably a mineral acid or hydrochloric acid (HCl) or dry hydrochloric acid. Exemplary carboxylic acids include, but are not limited to acetic acid, citric acid and formic acid. Exemplary mineral acids include, but are not limited to, hydrogen halides and there solutions (hydrofluoric acid, hydrochloric acid, hydrobromic acid, hydroiodic acid), halogen oxoacids (hypochlorous acid, chlorous acid, chloric acid, perchloric acid and corresponding bromine and iodine compounds), sulfuric acid, nitric acid, phosphoric acid, boric acid and the like.

In a preferred embodiment, the treating is performed in a non-polar solvent selected from the exemplary group including, but not limited to pentane, cyclopentane, hexane, cyclohexane, benzene, toluene, 1,4-dioxane, chloroform, diethyl ether, dichloromethane, most preferably diethyl ether. It is equally envisaged that the reaction may be adapted to be performed in a polar aprotic solvent, a polar protic solvent or mixtures thereof. In a preferred embodiment, the treating is performed at a temperature of 0-60° C., preferably 15-50° C., preferably 20-40° C., preferably 20-30° C., more preferably 25° C. or room temperature and has a reaction time determined by the passing of dry HCl into the reaction solution no longer producing a persistent turbidity, preferably less than 12 hr, preferably less than 8 hr, preferably less than 4 hr, preferably less than 2 hr, preferably less than 1 hr. In a preferred embodiment, the reaction has a yield of greater than 70%, preferably greater than 75%, preferably greater than 80%, more preferably greater than 85%, more preferably greater than 90%, most preferably greater than 95%.

In one step of the process, the monomer is cyclocopolymerized using a free radical initiator in a solvent in the presence of sulfur dioxide. The cyclocopolymerization protocols may be similar to those described in the literature with slight modifications as recognized as appropriate by a person of ordinary skill in the polymer chemistry art. In a preferred embodiment, the cyclocopolymerization is a Butler cyclopolymerization generally referring to polymerization of 1,6-dienes of diallyl quaternary ammonium salts to yield linear polymers containing rings along the linear chain and little or no residual unsaturation. The polymerization mechanism generally involves alternating intramolecular-intermolecular chain propagation. Thus, cyclopolymerization, as used herein, is any type of chain-growth addition polymerization that leads to introduction of cyclic structures into the main chain of the polymer. The reactions generally proceed under kinetic rather than thermodynamic control. Suitable monomers undergo cyclopolymerization by the use of appropriate initiators and well-known methods of radical initiation of polymerization.

As used herein a free radical initiator is a substance that can produce radical species under mild conditions and promote radical reactions. These substances generally possess weak bonds that have small bond dissociation energies and are often used in industrial processes such as polymer synthesis. Typical examples of radical initiators are halogen molecules, azo compounds and organic and inorganic peroxides. Halogens undergo the hemolytic fission relatively easily (i.e. chlorine gives to chlorine radicals (Cl.) by irradiation with ultraviolet light). Azo compounds (R—N=N—R') can be the precursor of two carbon centered radicals (R. and R'.) and nitrogen gas upon heating and/or by irradiation. Exemplary azo compound radical initiators include, but are not limited to, azobisisobutyronitrile (AIBN), 1,1'-azobis(cyclohexanecarbonitrile) (ABCN), 4,4'-azobis(4-cyanovaleric acid), 2,2'-azobis(2-methylpropionamidine) dihydrochloride, and 2,2'-azobis(2-methylpropionitrile). AIBN and ABCN yield isobutryonitrile and cyclohexanecarbonitrile radicals.

Organic peroxides each have a peroxide bond (—O—O—), which is readily cleaved to give two oxygen centered radicals. The oxyl radicals are unstable and believed to be transformed into relatively stable carbon centered radicals. Exemplary organic peroxide radical initiators include, but are not limited to, di-tert-butyl peroxide ($^t$BuOO$^t$Bu), benzoyl peroxide ((PhCOO)$_2$), methyl ethyl ketone peroxide, acetone peroxide, tert-butyl hydroperoxide, tert-butyl peracetate, cumene hydroperoxide, 2,5-Di(tert-butylperoxy)-2,5-dimethyl-3-hexyne, dicumyl peroxide, 2-butanone peroxide, tert-butyl peroxybenzoate, tert-butylperoxy 2-ethylhexyl carbonate, 2,5-bis(tert-butylperoxy)-2,5-dimethylhexane, lauroyl peroxide 1,1-bis(tert-butylperoxy)-3,3,5-trimethylcyclohexane, 2,4-pentanedione peroxide 1,1-bis(tert-butylperoxy)cyclohexane, and 1,1-bis(tert-amylperoxy)cyclohexane. Di-tert-butyl peroxide gives two t-butanoyl radicals ($^t$BuO.) and the radicals become methyl radicals (CH$_3$.) with the loss of acetone, benzoyl peroxide generates benzoyloxyl radicals (PhCOO.) each of which loses carbon dioxide to be converted into a phenyl radical (Ph.).

Inorganic peroxides function analogously to organic peroxides and many polymers are often produced from the alkenes upon initiation with peroxydisulfate salts. In solution, peroxydisulfate dissociates to give sulfate radicals (i.e. $[O_3SO—OSO_3]^{2-} \approx 2 [SO_4]^-$). Exemplary inorganic peroxide radical initiators include, but are not limited to, ammonium persulfate, hydroxymethanesulfinic acid monosodium salt dihydrate, potassium persulfate and sodium persulfate. In terms of the present disclosure, the free radical initiator may be a halogen, an azo compound, an organic peroxide, and inorganic peroxide or mixtures thereof, preferably an azo compound or organic peroxide, most preferably an azo compound, preferably AIBN and/or ABCN, most preferably azobisisobutyronitrile (AIBN).

In a non-limiting example, the cyclocopolymerization can be synthesized by initially dissolving a N,N-diallyl methionine-based monomer (compound of formula (II), such as compound 3) in solvent to form a polymer solution. Sulfur dioxide is then added to the polymer solution, for example by gas absorption such that the polymer solution contains sulfur dioxide and the N,N-diallyl methionine-based monomer in a molar ratio in the range of 1.5:1 to 1:1, preferably 1.3:1 to 1:1, preferably 1.25:1 to 1:1, preferably 1.2:1 to 1:1, preferably 1.15:1 to 1:1, preferably 1.1:1 to 1:1. In a preferred embodiment, the cyclcopolymerization is subsequently performed at a temperature of 0-80° C., preferably 20-75° C., preferably 30-70° C., preferably 40-65° C., preferably 45-60° C. or 60° C. and has a stirred reaction time of 2-48 hr, preferably 4-36 hr, preferably 8-30 hr, preferably 10-28 hr, preferably 12-24 hr, preferably 18-24 hr. In a preferred embodiment, the cyclocopolymerization reaction has a yield of greater than 50%, preferably greater than 60%, preferably greater than 65%, more preferably greater than 70%, more preferably greater than 75%.

In a preferred embodiment, the cyclocopolymerization is performed in a polar aprotic solvent, including but not limited, to tetrahydrofuran, ethyl acetone, dimethylformamide, acetonitrile, dimethyl sulfoxide and nitromethane or a polar protic solvent including formic acid, n-butanol, isopropanol, ethanol, methanol, and acetic acid or mixtures thereof. It is equally envisaged that the cyclocopolymerization may be adapted to be performed in a non-polar solvent. In a preferred embodiment, the cyclocopolymerization is performed in at least one solvent selected from the group consisting of dimethyl sulfoxide, ethanol and acetone. In a preferred embodiment, the solvent comprises dimethyl sulfoxide and the cyclocopolymerization reaction and the process produces the cyclopolymer of formula (I) wherein m and n are both whole numbers greater than zero such as compound 1. In a preferred embodiment, the solvent comprises ethanol and/or acetone and the cyclocopolymerization reaction and the process produces the cyclopolymer of formula (I) wherein m is a whole number greater than zero and n is equal to zero such as compound 2.

As used herein, "corrosion" refers to the natural process which converts refined metal to their more stable oxide. It is the gradual reduction of material (usually metals) by chemical reaction with their environment. Commonly, this means electrochemical oxidation of metal in reaction with an oxidant such as oxygen. Rusting, the formation of iron oxides is a well-known example of electrochemical corrosion producing oxide(s) or salt(s) of the original metal. Corrosion degrades the useful properties of materials and structures including strength, appearance and permeability to liquids and gases. Many structural alloys corrode merely from exposure to moisture in air, but the process can be strongly affected by exposure to certain substances. Corrosion can be concentrated locally to form a pit or crack, or it can extend across a wide area more or less uniformly corroding the surface. Because corrosion is a diffusion-controlled process, it occurs on exposed surfaces. Thus, methods to reduce the activity of the exposed surface, such as passivation and chromate conversion, can increase a material's corrosion resistance.

A corrosion inhibitor refers to a chemical compound or composition that when added to a liquid or a gas, decreases the corrosion rates of a material, typically a metal or an alloy. The effectiveness of a corrosion inhibitor depends on fluid composition, quantity of fluid and flow regime. A common mechanism for inhibiting corrosion involves formation of a coating, often a passivation layer, which prevents access of the corrosive substance to the metal. Corrosion inhibitors are often additives to the fluids that surround the metal or related object. The nature of the corrosive inhibitor depends on both the material being protected, which are most commonly metal objects and the corrosive agent(s) to be neutralized. Corrosive agents may include, but are not limited to, oxygen, hydrogen sulfide, and carbon dioxide.

In controlled environments (i.e. recirculating systems), corrosion inhibitors can often be added to act as reactive coatings. These chemicals, such as polymers or conducting polymers, form an electrically insulating or chemically impermeable coating on exposed metal surfaces, to suppress electrochemical reactions. Inhibition of metal corrosion by organic inhibitors is influenced by the presence of heteroatoms (N, O and S) as the inhibitor molecules interfere with anodic or cathodic reaction occurring on the metal surfaces arresting or minimizing corrosion processes. The greater polarizability of the lone pair of electrons in the third period elements makes them better inhibitors as a result of formation of coordinate-type bonds to cover and safeguard the metal surface. The trivalent amine and sulfide in the polymer background of the cyclopolymer of the present disclosure in any of its embodiments, as well as the residue of methionine keeping intact the integrity of its sulfide motifs and unquenched nitrogen valency (i.e. a trivalent N with its lone pair of electrons) may aid in arresting metal corrosion. Exemplary applications include, but are not limited to, metal piping systems, metals subjected to high temperature process, metals subjected to pH level extremes, engines, ball bearing, axles, boilers, air compressors, battery terminals or turbines.

According to a fourth aspect, the present disclosure relates to a method for determining a % inhibition efficiency of metal corrosion for the cyclopolymer of the present disclosure in any of its embodiments comprising i) weighing a first metal sample before immersion into a first aqueous acid solution to obtain a first blank weight ($FW_B$) and after immersion into the first aqueous acid solution to obtain a second blank weight ($SW_B$), ii) weighing a second metal sample substantially the same as the first metal sample before immersion into a second aqueous acid solution to obtain a first inhibitor weight ($FW_I$) and after immersion into the second aqueous acid solution to obtain a second inhibitor weight ($SW_I$), and iii) determining the % inhibition efficiency according to formula (III):

$$\text{Inhibition Efficiency }(\%) = \frac{(FW_B - SW_B) - (FW_I - SW_I)}{(FW_B - SW_B)} \times 100\% \quad \text{(III)}$$

wherein, the first aqueous acid solution and second aqueous acid solution are substantially the same except that the second aqueous acid solution comprises 0.1-125 ppm of the cyclopolymer of the present disclosure in any of its embodiments.

In a preferred embodiment, the first metal sample and the second metal sample are identical components of mild/low carbon steel or medium carbon steel having a carbon content of 0.01-0.6% by weight, preferably 0.05-0.3% by weight, more preferably 0.1-0.3% by weight. The components have general dimensions of 1.5-3.5×1.0-3.0×less than 0.5 cm$^3$. In a preferred embodiment, the first and second acidic solutions comprise 0.5-2.0 M HCl, preferably 0.75-1.5 M HCl, or 1.0 M HCl, and the only difference between the first and second acidic solution is that the second acidic solution comprises 0.1-125 ppm, preferably 0.1-100 ppm, preferably 0.25-50 ppm, preferably 0.5-25 ppm, preferably 1-20 ppm, preferably 1.25-10 ppm, preferably 2.5-5 ppm of the cyclopolymer of the present disclosure in any of its embodiments. In a preferred embodiment, the first metal samples and the second metal sample are immersed for 2-8 hours, preferably 4-7 hours or 6 hours at a temperature in the range of 20-100° C., preferably 40-80° C., preferably 50-70° C., or 60° C. The inhibition efficiencies (IEs) are determined as the average percent losses (preferably using triplicate determination with a standard deviation of less than 1.5%) and the relative weight loss method provides the % IEs in cases where the initial masses of the metal samples or components differ.

In a preferred embodiment, the cyclopolymer of formula (I) of the present disclosure in any of its embodiments has a corrosion inhibition efficiency (% IE) as determined above in the range of 25-99% when the cyclopolymer is contacted to a metal surface at a concentration ranging from 0.10-125 ppm of the cyclopolymer, preferably greater than 95% at a concentration of up to 100 ppm of the cyclopolymer, preferably greater than 95% at a concentration of up to 25 ppm of the cyclopolymer, preferably greater than 95% at a concentration of up to 10 ppm of the cyclopolymer, preferably greater than 95% at a concentration of up to 5 ppm of the cyclopolymer, preferably greater than 95% at a concentration of up to 2.5 ppm of the cyclopolymer, preferably greater than 90% at a concentration of up to 1.25 ppm of the cyclopolymer, preferably greater than 75% at a concentration of up to 0.65 ppm of the cyclopolymer, preferably greater than 60% at a concentration of up to 0.3 ppm of the cyclopolymer.

It is equally envisaged that the method described herein may be adapted to determine a % inhibition efficiency of metal corrosion for the N,N-diallyl methionine-based monomer of formula (II) in any of their embodiments. In this case, the only difference between the first and second acidic solutions is that the second acidic solutions is that the second acidic solution comprises 0.10-125 ppm of the monomer and none of the cyclopolymer is present in either acidic solution. In a preferred embodiment, the N, N-diallyl methionine-based monomer of formula (II) of the present disclosure in any of its embodiments has a corrosion inhibition efficiency (% IE) as determined above in the range of 25-95% when the N,N-dially methionine-based monomer is contacted to a metal surface at a concentration ranging from 0.10-125 ppm of the monomer, preferably greater than 95% at a concentration of up to 100 ppm of the monomer, preferably greater than 80% at a concentration of up to 25 ppm of the monomer, preferably greater than 70% at a concentration of up to 10 ppm of the monomer, preferably greater than 55% at a concentration of up to 5 ppm of the monomer, preferably greater than 40% at a concentration of up to 2.5 ppm of the monomer, preferably greater than 30% at a concentration of up to 1.25 ppm of the polymer.

Fractional inhibition efficiency (i.e. % IE/100), obtained from the weight loss measurements described herein is equated to surface coverage ($\theta$) values for the cyclopolymer molecules of the present disclosure on the metallic sample. The $\theta$ values obtained from weight loss measurements in 1.0 M HCl and the concentration in mol/L may be used to find the best fit among at least one adsorption isotherms selected from the group consisting of Temkin isotherms, Langmuir isotherms, Frumkin isotherms and Freundluich isotherms. In a preferred embodiment, the best fit as judged by the correlation coefficients is the Langmuir isotherm and the adsorption of the cyclopolymer of formula (I) of the present disclosure in any of its embodiments onto the metallic surface has a free energy of adsorption ($\Delta G°_{ads}$) in the range of $-30$ to $-70$ kJ mol$^{-1}$, preferably $-40$ to $-60$ kJ mol$^{-1}$, preferably $-42$ to $-58$ kJ mol$^{-1}$. In a preferred embodiment, the adsorption of the cyclopolymer of formula (I) of the present disclosure in any of its embodiments onto the metallic surface is a spontaneous process as indicated by the determined negative free energy of adsorption ($\Delta G°_{ads}$) which additionally indicates the prevalence of both electrostatic adsorption, physisorption, and chemisorption.

According to a fifth aspect, the present disclosure relates to a method for protecting metallic surfaces from corrosion, comprising treating the metal with the cyclopolymer of formula (I) of the present disclosure in any of its embodiments.

According to a sixth aspect, the present disclosure relates to a metallic material comprising cyclopolymer of formula (I) of the present disclosure in any of its embodiments, wherein the cyclopolymer is present in or on said metallic material.

In one embodiment, the cyclopolymer of formula (I) of the present disclosure in any of its embodiments may inhibit corrosion of at least one metal from the exemplary group including, but not limited to, copper, copper alloys (e.g. brass or bronze), aluminum alloys (e.g. aluminum-magnesium, nickel-aluminum, aluminum-silicon), nickel alloys (e.g. nickel-titanium or nickel chromium), carbon steels, alloy steels, stainless steels and tool steels, preferably one or more type of steel.

Steel is an alloy of iron and carbon that is widely used in construction and other applications because of its high tensile strength and low cost. Carbon, other elements, and inclusion within iron act as hardening agents that prevent the movement of dislocations that naturally exist in the iron atom crystal lattices. The carbon in typical steel alloys may contribute up to 2.1% of its weight. Steels can be broadly categorized into four groups based on their chemical compositions: carbon steels, alloy steels, stainless steels, and tool steels.

Carbon steels contain trace amounts of alloying elements and account for 90% of total steel production. Carbon steels can be further categorized into three groups depending on their carbon content: low carbon steels/mild steels contain up to 0.3% carbon, medium carbon steels contain 0.3-0.6% carbon, and high carbon steels contain more than 0.6% carbon. Alloy steels contain alloying elements (e.g. manganese, silicon, nickel, titanium, copper, chromium and aluminum) in vary proportions in order to manipulate the steel's properties, such as its hardenability, corrosion resistance, strength, formability, weldability or ductility. Stainless steels generally contain between 10-20% chromium as the main alloying element and are valued for high corrosion resistance. With over 11% chromium, steel is about 200 times more resistant to corrosion than mild steel. These steels can be divided into three groups based on their crystalline structure: austenitic steels, ferritic steels and martensitic steels. Tool steels contain tungsten, molybdenum, cobalt and vanadium in varying quantities to increase heat resistance and durability, making them ideal for cutting and drilling equipment.

Electrical impedance is the measure of opposition that a circuit presents to a current when a voltage is applied. Electrical impedance spectroscopy (EIS) has been applied to the study of corrosion systems and been proven to be a powerful and accurate method for measuring corrosion rates via the dielectric properties of a medium as a function of frequency. It is based on the interaction of an external field with the electric dipole moment of the sample. The resistance of the cyclopolymer described herein, is a measurement of impedance by applying Ohm's law to a reduction in current of an applied voltage, detected in the presence and absence of the cyclopolymer described herein. In a preferred embodiment, the cyclopolymer of the present disclosure or coatings, compositions, formulations, treatments or contacting thereof imparts an electrical impedance of 0.5-100$\Omega$, preferably 0.75-90Ω, preferably 1.0-85Ω, preferably 1.5-80Ω, preferably 2.0-75Ω, preferably 2.5-70Ω, preferably 5-65Ω, preferably 10-60Ω, preferably 20-50Ω, preferably 30-40Ω.

In a preferred embodiment, the cyclopolymer of the present disclosure may be present in a formulation or composition present as a coating. As used herein, a "coating" or "coat" refers to a covering that is applied to a surface of the metallic material to inhibit corrosion. The coating may substantially cover the metallic material (i.e at least 75% surface area coverage) and/or incompletely cover or only cover portions of the metallic material (i.e. less than 25% surface area coverage). The "coating" or "coat" may refer to one material (i.e. the cyclopolymer) that covers a material being coated, or alternatively the coating may refer to a plurality of materials further comprising a solvent, a dispersant, a surfactant, an inorganic corrosion inhibitor, an organic corrosion inhibitor, an anti-sealant compound or mixtures thereof. In a preferred embodiment, the coating, composition and/or formulation comprises at least 5%, at least 10%, at least 15%, at least 20%, at least 30%, at least 40%, preferably at least 50%, preferably at least 60%, preferably at least 70%, preferably at least 80%, preferably at least 85%, preferably at least 90%, preferably least 95% of the cyclopolymer of the present disclosure by weight relative to the total dry weight of the coating, composition and/or formulation. In another embodiment, the coating, composition and/or formulation may be further described as a paint, epoxy or varnish.

In a preferred embodiment, the treatment of the metallic material and the presence of the cyclopolymer may be achieved via dipping, brushing, spraying, painting or spin coating the metallic material with the cyclopolymer or compositions thereof. Dipping refers to a process in which an object or surface is immersed in the cyclopolymer to adhere the cyclopolymer to a surface of the metallic material, brushing refers to a bristle application, spraying refers to the use of an air pressurized nozzle for dispensing the cyclopolymer, painting refers to the use of rollers or spraying lacking air pressurization and spin coating refers to the uses of centrifugal force in applying the cyclopolymer. The application of the cyclopolymer and compositions may be followed by heat or UV treatment and may be to solidify or affix the cyclopolymer on the metallic material, as well as further treatments with other anti-corrosion materials.

The examples below are intended to further illustrate protocols for preparing and characterizing the compounds, monomers and polymers of the present disclosure. Further, they are intended to illustrate assessing the properties of these compounds, monomers and polymers. They are not intended to limit the scope of the claims.

Example 1

Materials and Characterization Methods

L-methionine ethyl ester hydrochloride and allyl bromide were purchased from Fluka AG and used as received without further purification. Potassium carbonate was purchased from sigma-Aldrich and used as received without further purification. Azobisisobutyronitrile (AIBN) from Fluka AG was crystallized from $CHCl_3$-EtOH. Dimethyl sulfoxide (DMSO) was dried and distilled (bp$_{4\ mmHg}$ 64-65° C.). Acetonitrile, diethyl ether, acetone and ethanol were purchased from Fluka AG and were used as received without further purification. Concentrated HCl was purchased from Fisher Scientific and was used to prepare 1 M HCl. Purified deionized water was used in all operations.

Elemental analyses and IR spectra were carried out on a Perkin Elmer Elemental Analyzer (Series II, Model 2400) and a Perkin Elmer FTIR (16F PC FTIR) spectrometer, respectively. The $^1H$ and $^{13}H$ NMR spectra have been measured on a JEOL LA 500 MHz spectrometer in $CDCl_3$, $D_2O$ or $CD_3OD$. An Ubbelohde viscometer (Viscometer Constant of 0.005718 cSt/s) was used for the measurements of viscositites using $CO_2$ free water under $N_2$ in order to avoid $CO_2$ absorption that may affect the viscosity data.

Example 2

Synthesis of N,N-Diallyl-1-methionine ethyl ester (Compound 5)

Methionine ester hydrochloride compound 4 upon reacting with allyl bromide gave its diallyl derivative compound 5. A mixture of compound 4 (16.0 g, 75 mmol), $K_2CO_3$ (31.0 g, 225 mmol), allyl bromide (19.1 g, 157.5 mmol) in acetonitrile (150 mL) under $N_2$ was stirred at 50° C. for 24 hr. The cooled mixture in ether (200 mL), after washing in water (3×75 mL), was dried and distilled using a vigreaux distilling column to obtain compound 5 (15 g, 78%), bp (2 mbar Hg) 110° C. Anal. calcd for $C_{13}H_{23}NO_2S$: C, 60.66; H, 9.01; N, 5.44; S, 12.46. found: C, 60.5; H, 8.9; N, 5.3; S, 12.2. $v_{max}$ (neat) 3078, 2979, 2917, 2838, 1729, 1641, 1450, 1368, 1160, 1115, 1027, 994, and 920 cm$^{-1}$; $\delta_H$ ($CDCl_3$) 1.29 (3H, t, J 7.0 Hz), 1.87 (1H, m), 1.97 (1H, m), 2.09 (3H, s), 2.56 (2H, m), 3.08 (2H, dd, J 7.6, 14.7 Hz), 3.34 (2H, m), 3.59 (1H, dd, J 6.1, 8.9 Hz), 4.17 (2H, m), 5.14 (4H, m), 5.76 (2H, m); $\delta_c$ ($CDCl_3$): 14.38 (1C, S$\underline{C}H_3$), 15.32 (1C, O$CH_2\underline{C}H_3$), 29.05 (1C, $\underline{C}H_2CH_2S$), 30.87 (1C, $CH_2\underline{C}H_2S$), 53.44 (2C, N$\underline{C}H_2$), 60.05 (1C, N$\underline{C}H$), 60.50 (1C, O$\underline{C}H_2$), 116.91 (2C, CH=$\underline{C}H_2$), 136.48 (2C, $\underline{C}H$=$CH_2$), 172.83 (1C, $\underline{C}O_2$), (77.00, middle C of $CDCl_3$).

Example 3

Synthesis of N,N-Diallyl-1-methionine ethyl ester hydrochloride (Compound 3)

Figure 2:
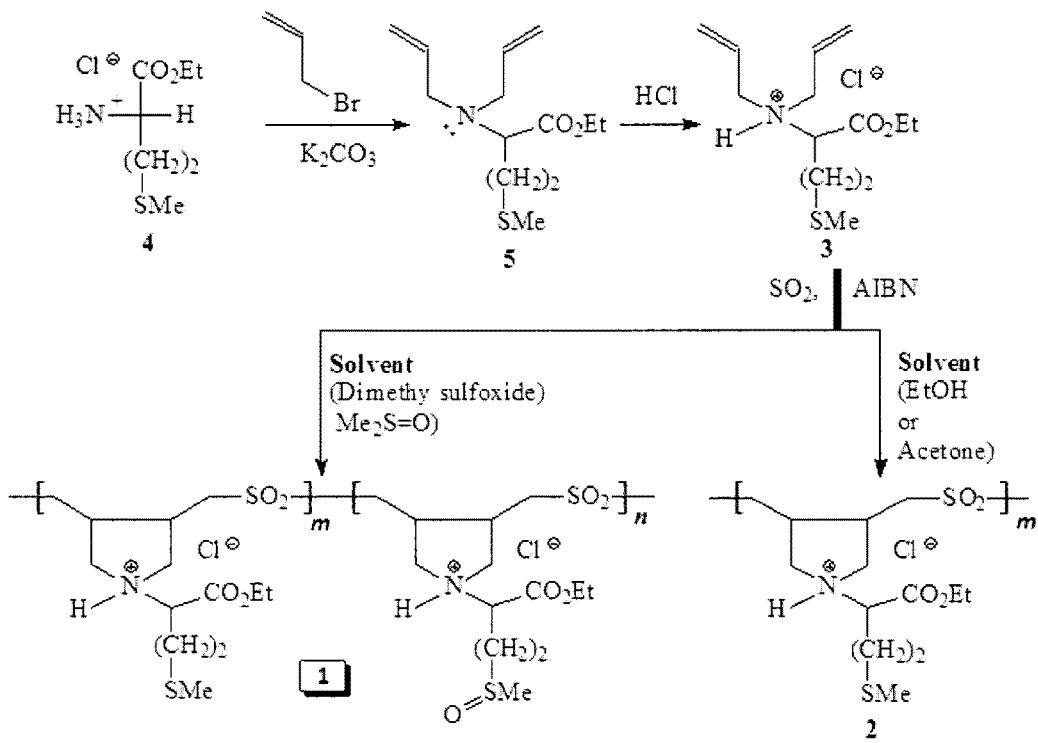
FIG. 2 is a synthetic scheme for the production of a cyclopolymer of formula (I), compound 1 and compound 2, from a N,N-diallyl methionine-based monomer compound 3, produced from a methionine-based salt compound 4, via a diallyl methionine-based compound 5.
Figure 3:
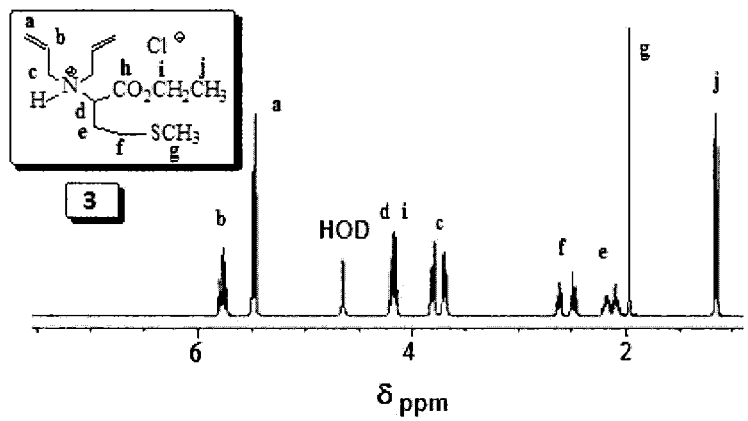
FIG. 3 is a $^1H$ nuclear magnetic resonance (NMR) spectra of the N,N-diallyl based methionine monomer of formula (II) that is compound 3 in $D_2O$.
Figure 6:
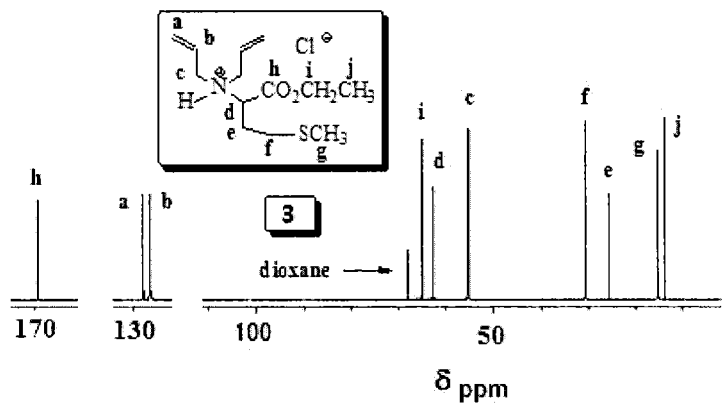
FIG. 6 is a $^{13}C$ nuclear magnetic resonance (NMR) spectra of the N,N-diallyl based methionine monomer of formula (II) that is compound 3 in $D_2O$.

Methionine ester hydrochloride compound 4 upon reacting with allyl bromide gave its diallyl derivative compound 5, which was converted into its hydrochloride salt compound 3 in excellent yield (FIG. 2). Dry HCl was passed onto a solution of amine compound 5 (13 g, 50.5 mmol) in ether (75 mL) until the supernatant liquid no longer was turbid due to the passage of HCl. The hydrochloride salt compound 5, separated as an oily liquid, was washed with ether (2×50 mL) to obtain N,N-Diallyl-1-methionine ethyl ester hydrochloride compound 5 (14.3 g, 96%). Anal. calcd for $C_{13}H_{24}ClNO_2S$: C, 53.14; H, 8.23; N, 4.77; S, 10.91. found: C, 52.9; H, 8.0; N, 4.7; S, 10.7. $v_{max.}$ (neat) 3418, 3085, 2981, 2919, 1741, 1644, 1427, 1374, 1288, 1204, 1163, 1004, 950, 855 and 777 cm$^{-1}$; $\delta_H$ ($D_2O$) 1.15 (3H, t, J 7.0 Hz), 1.97 (3H, s), 2.10 (1H, m), 2.18 (1H, m), 2.48 (1H, m), 2.62 (1H, m), 3.70 (2H, dd, J 7.3, 13.5 Hz), 3.81 (2H, dd, J 7.0, 13.7 Hz), 4.19 (3H, m), 5.48 (4H, m), 5.76 (2H, m), residual H in $D_2O$ at 4.65 ppm); $\delta_C$ ($D_2O$): 14.02 (1C, S$\underline{C}H_3$), 15.15 (1C, O$CH_2\underline{C}H_3$), 25.88 (1C, $\underline{C}H_2CH_2S$), 30.44 (1C, $CH_2\underline{C}H_2S$), 55.42 (2C, N$\underline{C}H_2$), 62.50 (1C, N$\underline{C}H$), 64.97 (1C, O$\underline{C}H_2$), 126.41 (2C, $\underline{C}H$=$CH_2$), 128.06 (2C, CH=$\underline{C}H_2$), 169.31 (1C, $\underline{C}O_2$), (67.4, dioxane). The $^1H$ and $^{13}C$ NMR spectra are displayed in FIG. 3 and FIG. 6, respectively. The DEPT-135 NMR analysis was also performed to confirm the $^{13}$C spectral assignments.

Example 4

Cyclocopolymerization of the monomer N,N-Diallyl-1-methionine ethyl ester hydrochloride (Compound 3) with $SO_2$ There were apprehensions about the polymerizability of the cationic monomer compound 3 under free radical conditions. In addition to the presence of degradative chain transfer allylic motifs [Shechter Y (1986) Selective oxidation and reduction of methionine residues in peptides and proteins by oxygen exchange between sulfoxide and sulfide. J. Biol. Chem 261:66-70; and Pike R M, Cohen R A (1960) Organophosphorus polymers. I. Peroxide-initiated polymerization of diethyl and diisopropyl vinylphosphonate. J. Polym. Sci 79:531-538. —each incorporated herein by reference in its entirety], the monomer also contained the sulfide functionality, which is a known chain transfer agent. However, the monomer readily underwent cyclocopolymerization with $SO_2$ using free radical initiator azobisisobutyronitrile (AIBN).

Of interesting note was the formation of cyclopolymer compound 1 (i.e. {3-sulfide-alt-$SO_2$}-ran-{3-sulfoxide-alt-$SO_2$}) in solvent DMSO while the cyclopolymer compound 2 (i.e. 3-sulfide-alt-$SO_2$) was obtained in the solvents ethanol or acetone. The details of the polymerizations including their intrinsic viscosities are given in Table 1. The formation of cyclopolymer compound 1 having sulfide and sulfoxide moieties in a 1:1 ratio is quite puzzling. While terpolymer compound 1 was found to be water soluble, copolymer compound 2 was water insoluble but soluble in methanol. The water solubility of the unexpected product cyclopolymer 1 was advantageous as the corrosion inhibition study demands its solubility in aqueous environment. The water solubility of cyclopolymer compound 1 could be attributed to the greater polarity of the sulfoxide motifs. This type of exchange of oxygen between sulfide and sulfoxide has been reported in the oxidation of methionine to methionine sulfoxide in the presence of DMSO/HCl.

TABLE 1

Monomer compound 3/$SO_2$ cyclocopolymerization[a] to cyclopolymer compound 1[i] and cyclopolymer compound 2[ii]

| Entry No. | Solvent (g) | AIBN (mg) | Yield (%) | Intrinsic Viscosity[b] (dL g$^{-1}$) |
|---|---|---|---|---|
| 1[i]  | DMSO (2)    | 100 | 75 | 0.235[c] |
| 2[ii] | Ethanol (2) | 100 | 72 | 0.176[d] |
| 3[ii] | Acetone (2) | 100 | 77 | 0.205[d] |

[a]Carried out using 7 mmol each of monomer compound 3 and SO2 in a solvent at 60° C. for 24 h.
[b]Viscosity of 0.125-1.0 wt % solution at 30° C. was measured with a Ubbelohde Viscometer (K = 0.005718 cSt/S).
[c]In 0.1M NaCl.
[d]In methanol.

Figure 9:
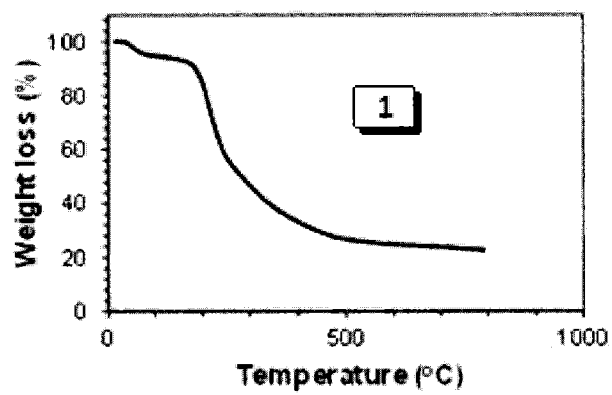
FIG. 9 is a thermal gravimetric analysis (TGA) curve of the cyclopolymer of formula (I) that is compound 1.
Figure 10:
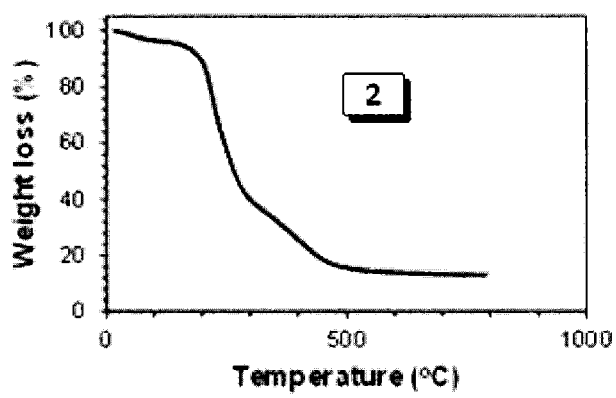
FIG. 10 is a TGA curve of the cyclopolymer of formula (I) that is compound 2.

The intrinsic viscosity [η] was obtained from viscosities of 0.125-1 wt % solutions at 30° C. using and Ubbelohde viscometer. The [η] values of the synthesized polymers were determined using Huggins viscosity relationship and found to be 0.235 (in 0.1 M NaCl), 0.176 and 0.205 (in methanol) dL g$^{-1}$, respectively (Table 1). Cyclopolymer compound 1 and cyclopolymer compound 2 were stable up to 210° C. as evident from the thermogravimetric analysis (TGA) curves (FIG. 9 and FIG. 10). Major loses could be attributed to the decomposition involving the release of $SO_2$.

Figure 4:
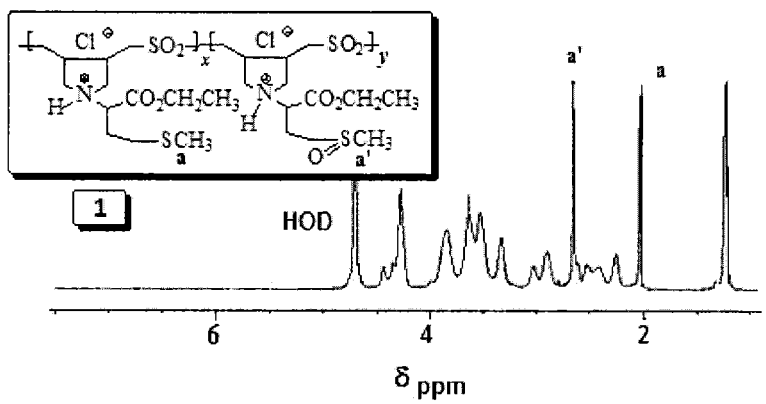
FIG. 4 is a $^1H$ NMR spectra of the cyclopolymer of formula (I) that is compound 1 in $D_2O$.
Figure 5:
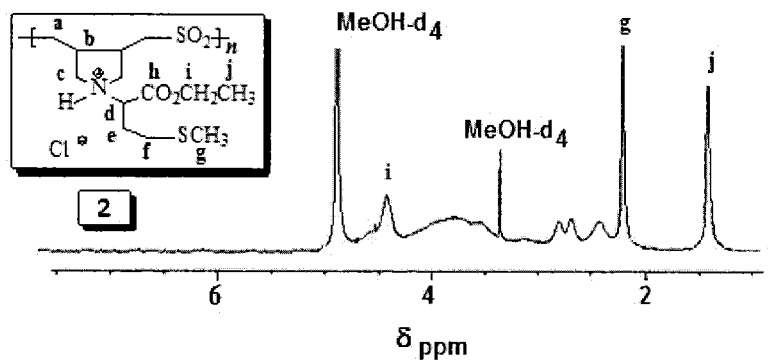
FIG. 5 is a $^1H$ NMR spectra of the cyclopolymer of formula (I) that is compound 2 in $CD_3OD$.
Figure 7:
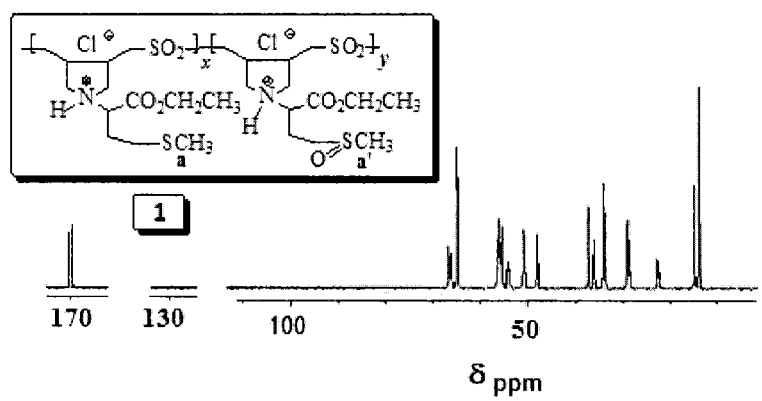
FIG. 7 is a $^{13}C$ NMR spectra of the cyclopolymer of formula (I) that is compound 1 in $D_2O$.
Figure 8:
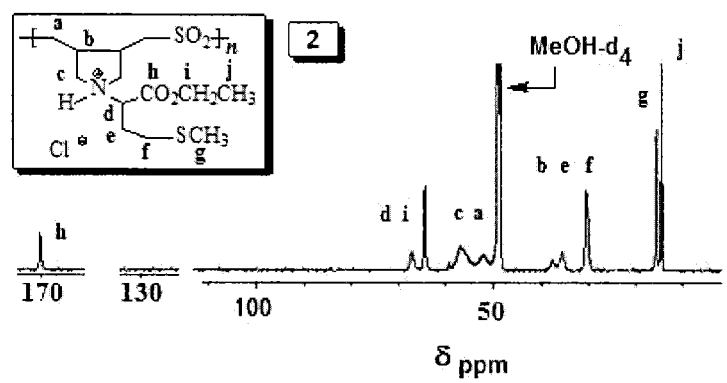
FIG. 8 is a $^{13}C$ NMR spectra of the cyclopolymer of formula (I) that is compound 2 in $CD_3OD$.

As described in Table 1, the detailed procedure adapted in entry 1 is as follows. After adsorption of $SO_2$ (7 mmol) in a solution of compound 3 (7 mmol) in DMSO (2 g), azobisisobutyronitrile (AIBN) (100 mg) was added. The mixture in a closed flask was stirred at 60° C. for 24 h. After precipitating in acetone, cyclopolymer compound 1 was dried in vacuo at 55° C. (6 h) (Yield 75%). When the polymerization was repeated in ethanol (2 g) or acetone (2 g), cyclopolymer compound 2 was obtained in 72 and 77% yields, respectively. Anal. calcd for 2: $C_{13}H_{24}ClNO_4S_2$: C, 43.63; H, 6.76; N, 3.91; S, 17.92%. found: C, 43.4; H, 6.6; N, 3.8; S, 17.7). $v_{max}$ (KBr) 3425, 2922, 2611 (br), 1740, 1633, 1450, 1377, 1308, 1219, 1128, 1014, 853 and 594 cm$^{-1}$. IR spectrum of 1 is almost identical to that of 2 except that an absorption at 1050 cm$^{-1}$ attributed to the S=O stretching absorption of 1; its elemental analysis supported the presence of sulfide and sulfoxide in a ratio of ≈1:1. The $^1$H and $^{13}$C NMR spectra of 1 are shown in FIG. 4 and FIG. 7, respectively, while those of 2 are displayed in FIG. 5 and FIG. 8. The thermal decomposition of 1 or 2: 240-250° C. (decomposed, turned black). The thermogravimetric analysis (TGA) curves of 1 and 2 are given in FIG. 9 and FIG. 10, respectively. It is envisaged that currently ongoing work to hydrolyze the ester functionalities in cyclopolymer compound 1 and cyclopolymer compound 2 may provide and/or convert them into potential anionic antiscalants [J. S. Gill J S (1999) A novel inhibitor for scale control in water desalination. Desalination 124:43-50; and David H, Hilla S, Alexander S (2011) State of the art of friendly "Green" scale control inhibitors: A review article. Ind. Eng. Chem. Res 50:7601-7607. —each incorporated herein by reference in its entirety].

Example 5

Figure 13:
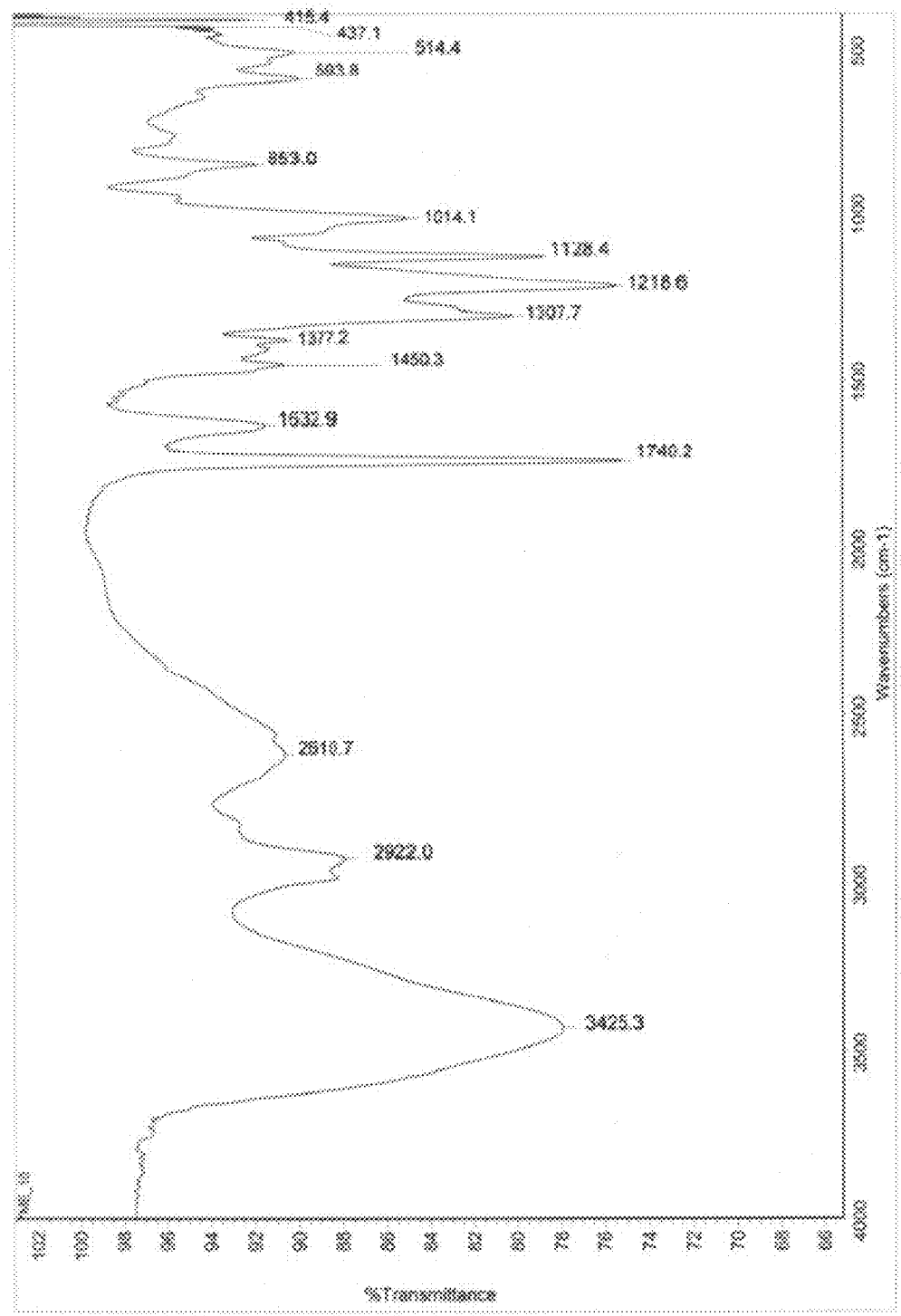
FIG. 13 is an infrared spectroscopy (IR) analysis of the cyclopolymer of formula (I) that is compound 2.

Fourier-Transform Infrared (FT-IR) Spectroscopy and Nuclear Magnetic Resonance (NMR) Analysis The absorption due to the $SO_2$ unit in cyclopolymer compound 1 and cyclopolymer compound 2 were assigned to the strong bands at ~1315 cm$^{-1}$ and ~1100 cm$^{-1}$, respectively, while a minor absorption at 1050 cm$^{-1}$ is attributed to the S=O stretching absorption in cyclopolymer compound 1. The presence of the ester functionality ($CO_2Et$) was confirmed by absorption peaks around 1740 cm$^{-1}$ (FIG. 13). The absence of any olefinic proton or carbon signals in the polymer spectra ascertains that the termination happens via chain transfer and/or coupling process (FIG. 4, FIG. 5, FIG. 7 and FIG. 8) [Butler G B, Angelo R J (1957) Preparation and polymerization of unsaturated quaternary ammonium compounds. Proposed intramolecular chain propagation. J. Am. Chem. Soc 79:3128-3131. —incorporated herein by reference in its entirety]. The proton spectrum of cyclopolymer compound 1 shows the presence of two types of $CH_3$ signals in a and a' in FIG. 4 attributed to the presence of sulfide (S—$CH_3$) and stronger electron-withdrawing sulfoxide motifs [S(=O)$CH_3$]. The two $^{13}$C signals around 170 ppm are attributed to two different carbonyl groups in the repeat units of cyclopolymer compound 1 (FIG. 7). $^{13}$C NMR assignments are based on previous works on Butler's cyclopolymers.

Example 6

Corrosion Inhibition Tests

For gravimetric measurements, the coupons of mild steel have the composition (wt %): 0.082% (C), 0.032% (Si), 0.207% (Mn), 0.016% (Cr), 0.062% (Ni), 0.012% (Mo), 0.045% (Al), 0.029% (Cu), 0.042% (W), 0.014% (Pb), 0.048% (Sn), 0.017% (Zn), 0.027% (As), <0.019% (N), <99.3% (Fe).

The Inhibition Efficiencies (IEs) were determined as described elsewhere [Annand R R, Hurd R M, Hackerman N (1965) Adsorption of Monomeric and Polymeric Amino Corrosion Inhibitors on Steel. J. Electrochem. Soc 112:138-144; and Bacskai R, Schroeder A H, Young D C (1991) Hydrocarbon-soluble alkaline/formalin/formaldehyde oligomers as corrosion inhibitors. J. Appl. Polym. Sci 42:2435-2441; and Ali S A, Saeed M T, Rahman S U (2003), The isoxazolidines: a new class of corrosion inhibitors of mild steel in acidic medium. Corros. Sci 45:253-266. —each incorporated herein by reference in its entirety] after immersing steel coupons having dimension of 2.5×2.0×0.1 cm$^3$ into 1.0 M HCl (Fisher Scientific Company (250 cm$^3$) containing 0 (blank) or various amounts (>0-100 ppm) of the inhibitors at 60° C. for 6 h. The IE was obtained using the equation of formula (III):

$$\text{Inhibition Efficiency (\%)} = \frac{(FW_B - SW_B) - (FW_I - SW_I)}{(FW_B - SW_B)} \times 100\% \quad (III)$$

The average percent losses were used (triplicate determinations, standard deviation: 0.4-1.5%). The relative weight loss method [Ali S A, Al-Muallem H A, Rahman S U, Saeed M T (2008) Hydrophobic-tailed bicycloisoxazolidines: A comparative study of the newly synthesized compounds on the inhibition of mild steel corrosion in hydrochloric and sulfuric acid media. Corros. Sci 50:664-675; and Ali S A, Al-Muallem H A, Rahman S U, Saeed M T (2008) Bis-isoxazolidines: A new class of corrosion inhibitors of mild steel in acidic medium. Corros. Sci. 50:3070-3077. —each incorporated herein by reference in its entirety] was used to determine the % Inhibition Efficiencies in cases where the initial masses of the coupons differed.

The results of the % Inhibition Efficiency (Table 2) of mild steel corrosion at 60° C. in 1.0 M HCl revealed that cyclopolymer compound 1 gave much higher protection than its monomer compound 3 or methionine compound 6 or methionine compound 4. It is an amazing performance by the novel cyclopolymer. The inhibition efficiency of 99% was achieved at a concentration of 25 ppm, while at a relatively small concentration of 1.25 ppm, a % inhibition efficiency of 93% was achieved. The polymer having multiple adsorption sites gave superior protection than its monomeric counterpart compound 3 (% IE of 31% at 1.25 ppm.

Figure 11:
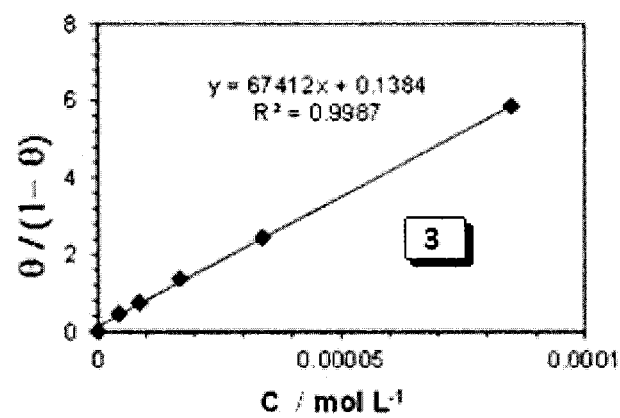
FIG. 11 is a Langmuir adsorption isotherm of the N,N-diallyl based methionine monomer of formula (II) that is compound 3 in 1.0 M HCl at 60° C.
Figure 12:
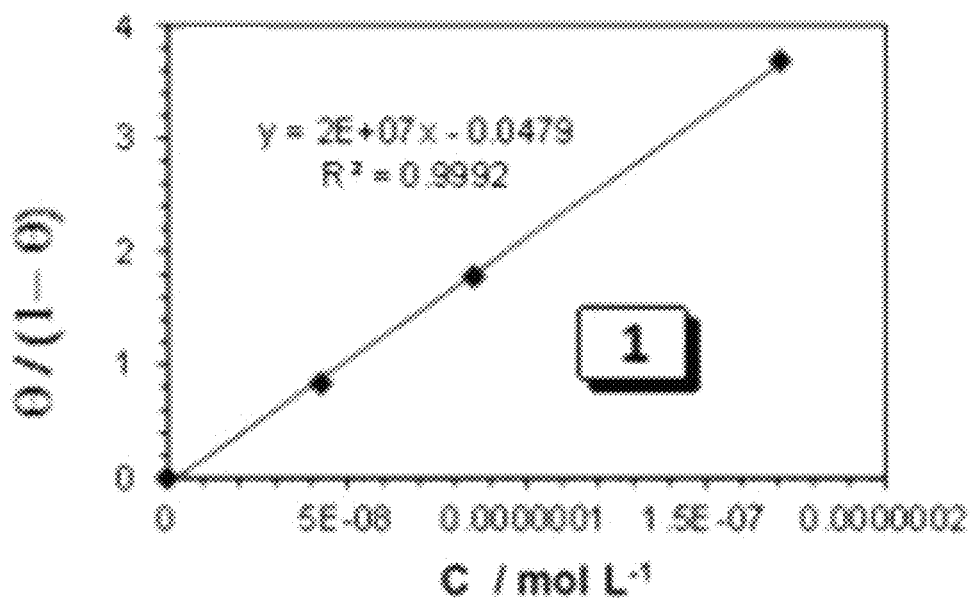
FIG. 12 is a Langmuir adsorption isotherm of cyclopolymer of formula (I) that is compound 1 in 1.0 M HCl at 60° C.

Temkin ($K_{ads}C=e^{f\theta}$), ii) Langmuir ($\theta/(1-\theta)=K_{ads}C$), iii) Frumkin ($K_{ads}C=\theta/(1-\theta)e^{-2a\theta}$), and iv) $\theta=K_{ads}C^n$) [Frumkin A (1925) Electrocapillary curve of higher aliphatic acids and the state equation of the surface layer. Z. Phys. Chem 116:466-484; and Bockris J O'M, Khan S U M (1993) Surface Electrochemistry: A Molecular Level Approach, Plenum Press, New York, N.Y., USA. —each incorporated herein by reference in its entirety]. For both monomer compound 3 and cyclopolymer compound 1, the Langmuir isotherms became the best fit as revealed by the correlation coefficients (FIG. 11 and FIG. 12). The equilibrium constant $K_{ads}$ and the free energy of adsorption ($\Delta G°_{ads}$) are related by the equation having formula (V):

$$K_{ads} = \frac{1}{55.5} e^{\frac{-\Delta G°_{ads}}{RT}} \quad (V)$$

The $K_{ads}$ for the adsorption of monomer compound 3 and cyclopolymer compound 1 were determined to be 67412 and 2.00×10$^7$ L mol$^{-1}$, respectively, leading to the corresponding $\Delta G°_{ads}$ values of −41.0 and −57.7 kJ mol$^{-1}$ (Table 3). Generally, $\Delta G°_{ads}$ up to −20 kJ mol$^{-1}$ and in the range of −80 to −400 kJ mol$^{-1}$ are attributed to physisorption and chemisorption, respectively. The chemisorption occurs because of formation of coordinate type of bonds by sharing electrons of the inhibitor molecules and the vacant orbital on the metal surface. The calculated $\Delta G°_{ads}$ values at −41.9 kJ mol$^{-1}$ for monomer compound 3 and −57.7 kJ mol$^{-1}$ for cyclopolymer compound 1 indicate the prevalence of both electrostatic adsorption and chemisorption [Duan S Z, Tao Y L (1990) Interface chemistry, Higher Education Press, Beijing, China; and Bransoi V, Baibarac M, Bransoi F (2001) International Congress of Chemistry and Chemical Engineering, Romania—each incorporated herein by reference in its entirety]. The presence of π-electrons, sulfide and sulfoxide in cyclopolymer compound 1 may interact with the d-orbitals of iron or accumulated Fe$^{2+}$ on the anodic sites to form a coordinate type of bond.

TABLE 2

Inhibition efficiency (% IE) in the presence of various ppm of inhibitor molecules to arrest corrosion of mild steel in 1.0M HCl (6 h, 60° C.)

| | (% IE at ppm of compounds) | | | | | | | | |
|---|---|---|---|---|---|---|---|---|---|
| Compound | 0.16 | 0.31 | 0.63 | 1.25 | 2.5 | 5 | 10 | 25 | 100 |
| Compound 6 | — | — | — | — | — | — | — | — | 72 |
| Compound 4 | — | — | — | — | — | 57 | — | — | 87 |
| Compound 3 | — | — | — | 31 | 43 | 58 | 71 | 85 | 94 |
| Compound 1 | 45 | 64 | 79 | 93 | 95 | 96 | 97 | 99 | 99 |

Example 7

Adsorption Isotherms

Fractional inhibition efficiency (i.e. % IE/100), obtained from the weight loss measurements, is equated to surface coverage (θ) values for the inhibitor molecules (Table 2). The θ values obtained from weight loss measurement in 1.0 M HCl and C (the concentration in mol/L) were used to find the best fit among the following adsorption isotherms: i)

TABLE 3

The values of the adsorption equilibrium constant and free energy from Langmuir adsorption isotherms

| Compound | $K_{ads}$ (L mol$^{-1}$) | $\Delta G°_{ads}$ (kJ mol$^{-1}$) |
|---|---|---|
| Compound 3 | 67412 | −41.9 |
| Compound 1 | 20.00 × 10$^7$ | −57.7 |

The invention claimed is:

1. A cyclopolymer of formula (I)

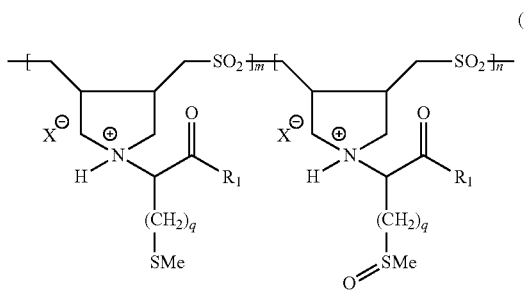

(I)

or a salt, solvate, tautomer, or stereoisomer thereof;
wherein $R_1$ is —H, —OH, —$NH_2$, —$OR_2$, —$NHR_2$, or —$NR_2R_3$;
$R_2$ and $R_3$ are independently an optionally substituted alkyl, optionally substituted cycloalkyl, or optionally substituted aryl;
m is a whole number greater than zero;
n is a whole number greater than or equal to zero;
q is a whole number in the range of 1-10; and
X is a counter ion.

2. The cyclopolymer of claim 1, wherein the compound of formula (I) is

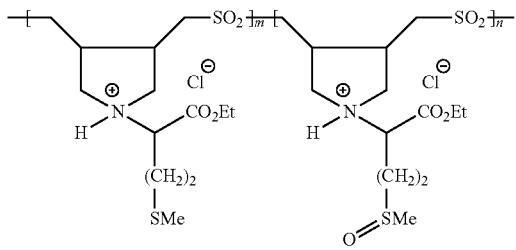

wherein m and n are independently whole numbers greater than zero.

3. The cyclopolymer of claim 2, wherein m is a whole number greater than zero and n is equal to zero.

4. The cyclopolymer of claim 1, wherein the ratio of m:n is in the range of 10:1 to 1:10.

5. The cyclopolymer of claim 1, which has an intrinsic viscosity in the range of 0.125-0.300 dL $g^{-1}$ in a solution comprising 0.125-1 wt % of the cyclopolymer relative to the total weight of the solution.

6. The cyclopolymer of claim 1, which is soluble in water, soluble in methanol, or both.

7. The cyclopolymer of claim 1, which has a corrosion inhibition efficiency (% IE) in the range of 25-99% when the cyclopolymer is contacted to a metal surface at a concentration ranging from 0.10-125 ppm.

8. The cyclopolymer of claim 1, which has a free energy of adsorption ($\Delta G°_{ads}$) in the range of −30 to −70 kJ $mol^{-1}$ by a Langmuir adsorption isotherm.

9. A process for producing the cyclopolymer of claim 1, comprising:
reacting a methionine-based salt with an allyl halide to form a diallyl methionine compound;
treating the diallyl methionine compound with an acid to form a N,N-diallyl methionine-based monomer; and
cyclocopolymerizing the N,N-diallyl methionine-based monomer using a free radical initiator in a solvent in the presence of sulfur dioxide.

10. The process of claim 9, wherein the cyclocopolymerizing is a Butler cyclopolymerization reaction and the free radical initiator is azobisisobutyronitrile (AIBN).

11. The process of claim 9, wherein the solvent comprises dimethyl sulfoxide and the process produces the cyclopolymer of formula (I) wherein m and n are independently whole numbers greater than zero.

12. The process of claim 9, wherein the solvent comprises ethanol, acetone, or both and the process produces the cyclopolymer of formula (I) wherein m is a whole number greater than zero and n is equal to zero.

13. A method for protecting metallic surfaces from corrosion, comprising treating the metal with the cyclocopolymer of claim 1.

14. A metallic material comprising the cyclopolymer of claim 1, wherein the cyclopolymer is present in or on said metallic material.

* * * * *

UNITED STATES PATENT AND TRADEMARK OFFICE
CERTIFICATE OF CORRECTION

PATENT NO. : 9,556,301 B1
APPLICATION NO. : 14/957150
DATED : January 31, 2017
INVENTOR(S) : Mohammad Abu Jafar Mazumder et al.

It is certified that error appears in the above-identified patent and that said Letters Patent is hereby corrected as shown below:

On the Title Page

Item (73), the Assignee's information has been listed incorrectly. Item (73) should read:
-- (73) Assignee: King Fahd University of Petroleum and Minerals, Dhahran (SA) --

Signed and Sealed this
Tenth Day of April, 2018

Andrei Iancu
*Director of the United States Patent and Trademark Office*